US012600957B2

(12) United States Patent
Zhu et al.

(10) Patent No.: US 12,600,957 B2
(45) Date of Patent: Apr. 14, 2026

(54) SYNTHESIS OF TRANSCRIPTS USING VSW-3 RNA POLYMERASE

(71) Applicant: RNASYN BIOTECH. CO., LTD., Hubei (CN)

(72) Inventors: Bin Zhu, Wuhan (CN); Heng Xia, Wuhan (CN)

(73) Assignee: RNAsyn Biotech. Co., Ltd. (CN)

( * ) Notice: Subject to any disclaimer, the term of this patent is extended or adjusted under 35 U.S.C. 154(b) by 1177 days.

(21) Appl. No.: 17/614,174

(22) PCT Filed: Jul. 24, 2020

(86) PCT No.: PCT/CN2020/104345
§ 371 (c)(1),
(2) Date: Nov. 24, 2021

(87) PCT Pub. No.: WO2020/239144
PCT Pub. Date: Dec. 3, 2020

(65) Prior Publication Data
US 2022/0220459 A1 Jul. 14, 2022

(30) Foreign Application Priority Data

May 24, 2019 (CN) .......................... 201910440379.0
May 24, 2019 (CN) .......................... 201910440391.1

(51) Int. Cl.
*C12N 9/12* (2006.01)
*C12N 9/22* (2006.01)
*C12P 19/34* (2006.01)

(52) U.S. Cl.
CPC ............. *C12N 9/1247* (2013.01); *C12N 9/22* (2013.01); *C12P 19/34* (2013.01); *C12Y 207/07006* (2013.01)

(58) Field of Classification Search
CPC ...................... C12N 9/1247; C12Y 207/07006
See application file for complete search history.

(56) References Cited

U.S. PATENT DOCUMENTS 11,066,655 B2 * 7/2021 Richardson .... C12Y 207/07006

FOREIGN PATENT DOCUMENTS

CN 108018271 A 5/2011

OTHER PUBLICATIONS

Solovyev, Victor V., and Ilham A. Shahmuradov. "PromH: promoters identification using orthologous genomic sequences." Nucleic acids research 31.13 (2003): 3540-3545 (Year: 2003).*
GENBANK, Pseudomonas phage VSW-3, complete genome, NCBI Reference Sequence: NC_041885.1 (May 2, 2019), available at: https://www.ncbi.nlm.nih.gov/nuccore/1631918249?sat=48&satkey=135616115 (last visited Mar. 7, 2023), US.
International Searching Authority, International Search Report, PCT Application No. PCT/CN2020/104345, dated Oct. 10, 2020, CN.
International Searching Authority, Written Opinion of the International Searching Authority, PCT Application No. PCT/CN2020/104345, dated Oct. 10, 2020, CN.
Zhang et al., Complete Genome Sequence of the Lytic Cold-Active Pseudomonas fluorescens bacteriophage VSW-3 from Napahai plateau wetland, Virus Genes 53(1), Oct. 31, 2016, Springer Publishing, US.
Zhang, Biological Characteristics and Comparative Genomics Analysis of Cold-active Phage VSW-3 Infecting Pseudomonas Fluorescents, Chinese Master's Theses Full-text Database, Basic Sciences 1: Abstract, Chapter 2.3, and Chapter 3.3, Jan. 15, 2018, CN.
Zhang et al., Sequence ID: ANH51091.1, GenBank, Jun. 2, 2016, National Institutes of Health, US.

* cited by examiner

*Primary Examiner* — Robert J Yamasaki
(74) *Attorney, Agent, or Firm* — Reichel Stohry Dean LLP; Natalie J. Dean

(57) ABSTRACT

The present disclosure provided a RNA polymerase from a psychrophilic bacteriophage VSW-3. The RNA polymerase retains its RNA polymerase activity at low temperature (e.g., as low as 4° C.), is not sensitive to Class II transcription terminator, does not produce 3' cis extension in the transcripts, and generates transcripts without detectable dsRNA contamination.

13 Claims, 11 Drawing Sheets

Specification includes a Sequence Listing.

SYNTHESIS OF TRANSCRIPTS USING VSW-3 RNA POLYMERASE

PRIORITY

This patent application is related to, claims the priority benefit of, and is a 35 U.S.C. 371 national stage application of International Patent Application Serial No. PCT/CN2020/ 104345 filed Jul. 24, 2020, which relates to and claims the priority benefit of: (a) Chinese Patent Application No. 201910440379.0 filed May 24, 2019, and (b) Chinese Patent Application No. 201910440391.1 filed May 24, 2019. The entire contents of each of the aforementioned priority applications are hereby expressly incorporated herein by reference in their entireties-into this disclosure.

FIELD OF THE INVENTION

The present disclosure generally relates to an RNA polymerase from VSW-3 phage. The present disclosure also relates to the uses of the RNA polymerase for in vitro transcription (IVT).

BRIEF DESCRIPTION OF THE SEQUENCE LISTINGS

The sequences described herein are also provided in computer readable form encoded in a file filed herewith and which is herein incorporated by reference. The information recorded in computer readable form is identical to the written Sequence Listings provided herein, pursuant to 37 C.F.R. § 1.821(f).

BACKGROUND

Bacteriophages are the most abundant and diverse organisms on earth, and can survive in various extreme environments. Biotechnology requires diverse and efficient molecular tools for nucleic acid manipulation and phage proteins are always good candidates due to their simplicity and high efficiency. Recently, genome sequencing and bioinformatics studies have revealed some psychrophilic phages from polar regions, deep seas, glaciers and plateau wetlands on earth. VSW-3 phage is one of the lytic cold-active phages that infect *Pseudomonas fluorescens* SW-3 cells from the Napahai wetland in China, and some of its proteins were predicted to have cold-activities in nucleic acids metabolism including transcription, DNA replication, and recombination.

For decades, there are only several types of RNA polymerase (RNAP) available (T7, SP6 and the newly discovered Syn5 RNAP) for in vitro enzymatic transcription, and there are some difficult problems that need to be overcome. The first is about abolished transcripts. When there are Class I or Class II terminators in the DNA template, T7 RNAP will partially stop at both Class I and Class II terminators. Syn5 RNAP is the first RNAP that won't stop at Class I terminator but the interruption will be more severe when encountering class II terminator. The second is that transcripts of T7 RNAP contain double-stranded RNA (dsRNA) that will induce severe nucleic-acid immune response in vivo, so people have tried various ways to reduce the immunogenicity of these RNAs including HPLC purification and modifications (5mC, 5moU and PseudoU, et al.). In the end, since there are nonspecific self-primed elongations at RNA's 3'-terminal, making T7 RNAP and Syn5 RNAP not suitable for the synthesis of short RNAs like siRNA or sgRNA.

SUMMARY

In one aspect, the present disclosure provides an RNA polymerase comprising a polypeptide which comprises
1) an amino acid sequence of SEQ ID NO:5, or
2) an amino acid sequence having at least 80% sequence identity to SEQ ID NO:5 and possessing a RNA polymerase activity.

In some embodiments, the RNA polymerase is isolated from a psychrophilic bacteriophage, or is encoded by a gene of a psychrophilic bacteriophage.

In some embodiments, the psychrophilic bacteriophage is bacteriophage VSW-3.

In some embodiments, the RNA polymerase comprises an amino acid sequence of SEQ ID NO:6.

In some embodiments, the RNA polymerase possesses a RNA polymerase activity under 4-37° C.

In some embodiments, the RNA polymerase comprises a protein tag having a sequence of SEQ ID NO: 13.

In some embodiments, the promoter sequence for the RNA polymerase has the sequence of SEQ ID NO: 1, 2, 3 or 4.

In another aspect, the present disclosure provides a method for preparing the RNA polymerase, which comprises expressing the RNA polymerase in a host cell at 10-15° C.

In another aspect, the present disclosure provides a method for performing a transcription reaction, which comprises incubating an RNA polymerase with a DNA molecule and nucleotides for a sufficient time to produce transcripts, wherein the RNA polymerase comprises a polypeptide comprising
1) an amino acid sequence of SEQ ID NO:5, or
2) an amino acid sequence having at least 80% sequence identity to SEQ ID NO:5 and possessing an RNA polymerase activity,
and wherein the DNA molecule comprises a promoter sequence for the RNA polymerase and a DNA sequence to be transcribed.

In some embodiments, the RNA polymerase is isolated from a psychrophilic bacteriophage, or is encoded by a gene of a psychrophilic bacteriophage.

In some embodiments, the psychrophilic bacteriophage is bacteriophage VSW-3.

In some embodiments, the RNA polymerase comprises an amino acid sequence of SEQ ID NO:6.

In some embodiments, the incubating is performed at 4-37° C.

In some embodiments, the incubating is performed at 25° C.

In some embodiments, the incubating is performed at 25° C. for 12 h.

In some embodiments, the promoter sequence for the RNA polymerase has a nucleotide sequence of SEQ ID NO: 1, 2, 3 or 4.

In some embodiments, the incubating is performed in a buffer containing 5 mM DTT.

In some embodiments, the incubating is performed in a buffer containing: 40 mM Tris-HCl (pH 8.0), 16 mM $MgCl_2$, 2 mM spermidine, 5 mM DTT, and 4 mM NTPs.

In some embodiments, the RNA polymerase in the buffer is 0.15 µM.

In some embodiments, a class II transcription terminator sequence ATCTGTT does not mediate a transcriptional termination of the transcription reaction.

In some embodiments, the DNA sequence to be transcribed comprises a coding sequence for Cas9.

In some embodiments, the coding sequence comprises a nucleotide sequence of SEQ ID NO: 8.

In some embodiments, the nucleotides comprise pseudoUTP, 5mCTP and/or 5moUTP.

In some embodiments, the nucleotides comprise mSCTP, m6ATP, 2'-F-dATP and/or 2'-F-dUTP.

In some embodiments, the RNA polymerase comprises an amino acid sequence of SEQ ID NO:6, and the nucleotides comprises 2'-F-dATP and/or 2'-F-dUTP.

In some embodiments, the transcript is mRNA.

In some embodiments, the transcript is sgRNA.

In some embodiments, the transcript has no 3' cis extension.

In some embodiments, the transcript has no detectable dsRNA contamination.

In another aspect, the present disclosure provides a kit for transcription comprising the RNA polymerase.

The RNA polymerase retains its RNA polymerase activity at low temperature (e.g., as low as 4° C.), is not sensitive to Class II transcription terminator, does not produce 3' cis extension in the transcripts, and generates transcripts without detectable dsRNA contamination.

DETAILED DESCRIPTION

Figure 1:
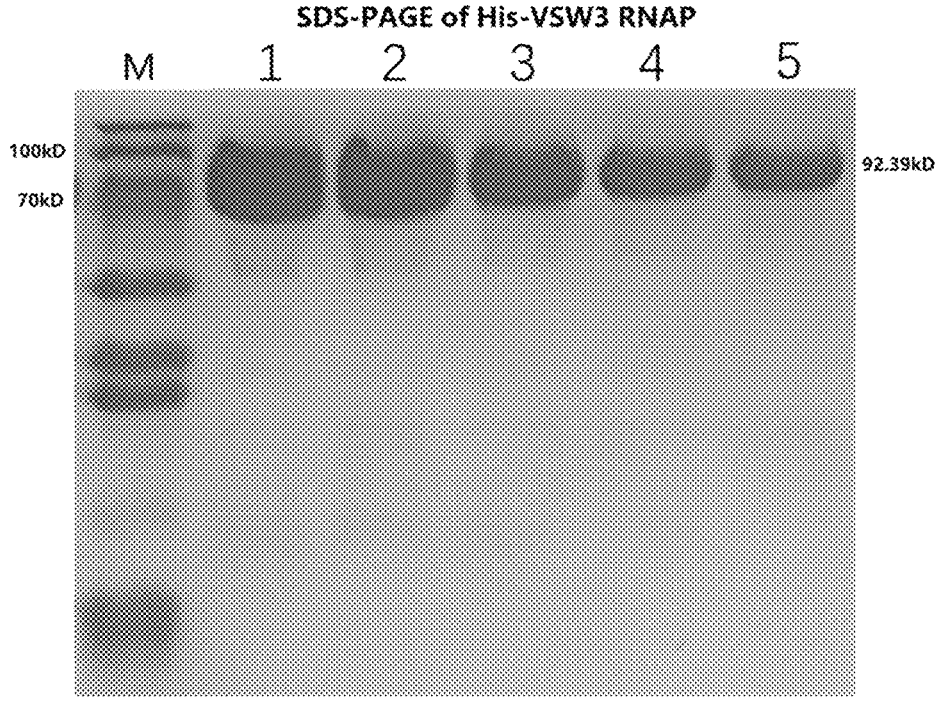
FIG. 1. Protein expression and purification of VSW-3 RNAP. The concentration of VSW-3 RNAP has been measured with Bradford method. In SDS-PAGE gel, proteins were stained with Coomassie Blue. According to grayscale value, the final working concentration of T7 RNAP (New England Biolabs, #M02515) is about 0.15 μM.

Unless defined otherwise, technical and scientific terms used herein have the same meaning as commonly understood by a person of ordinary skill in the art. Any methods, devices and materials similar or equivalent to those described herein can be used in the practice of this invention. The following definitions are provided to facilitate understanding of certain terms used frequently herein and are not meant to limit the scope of the present disclosure.

As used herein, "a promoter sequence for the RNA polymerase" refers to a DNA sequence which define where transcription of a gene or a coding sequence by the RNA polymerase begins. Promoter sequences are typically located directly upstream or at the 5' end of the transcription initiation site.

As used herein, "3' cis extension" refers to a 3' non-templated addition when performing an in vitro transcription reaction with an RNA polymerase, especially, T7 RNAP. T7 RNAP possesses an RNA-dependent RNA polymerase activity that can result in non-templated hairpin RNAs as byproducts of the transcription reaction, often necessitating purification by denaturing polyacrylamide gel electrophoresis to isolate the intended RNA products.

As used herein, the terms "nucleic acid molecule" and "nucleic acid sequence" are used interchangeably and are intended to include, but are not limited to, a polymeric form of nucleotides that may have various lengths, either deoxy-ribonucleotides or ribonucleotides, or analogs thereof. Nucleic acid molecules include single-stranded DNA (ssDNA), double-stranded DNA (dsDNA), single-stranded RNA (ssRNA) and double-stranded RNA (dsRNA). Different nucleic acid molecules may have different three-dimensional structures, and may perform various functions, known or unknown. Non-limiting examples of nucleic acid molecules include a gene, a gene fragment, a genomic gap, an exon, an intron, intergenic DNA (including, without limitation, heterochromatic DNA), messenger RNA (mRNA), transfer RNA (tRNA), ribosomal RNA (rRNA), ribozymes, small interfering RNA (siRNA), miRNA, small nucleolar RNA (snoRNA), cDNA, recombinant polynucleotides, branched polynucleotides, plasmids, vectors, isolated DNA of a sequence, isolated RNA of a sequence, nucleic acid probes, and primers. Nucleic acid molecules useful in the methods described herein may comprise natural nucleic acid sequences and variants thereof, artificial nucleic acid sequences, or a combination of such sequences.

An oligonucleotide sequence refers to a linear polymer of natural or modified nucleosidic monomers linked by phosphodiester bonds or analogs thereof. The term "oligonucleotide" usually refers to a shorter polymer, e.g., comprising from about 3 to about 100 monomers, and the term "polynucleotide" usually refers to longer polymers, e.g., comprising from about 100 monomers to many thousands of monomers. An "oligonucleotide fragment" refers to an oligonucleotide sequence that has been cleaved into two or more smaller oligonucleotide sequences. Oligonucleotides comprising probes or primers usually have lengths in the range of from 12 to 60 nucleotides, and more usually, from 18 to 40 nucleotides. Oligonucleotides and polynucleotides may be natural or synthetic. Oligonucleotides and polynucleotides include deoxyribonucleotides, ribonucleotides, and non-natural analogs thereof. Such as anomeric forms thereof, peptide nucleic acids (PNAS), and the like, provided that they are capable of specifically binding to a target genome by way of a regular pattern of monomer-to-monomer interactions, such as Watson-Crick type of base pairing, base stacking, Hoogsteen or reverse Hoogsteen types of base pairing, or the like.

Usually nucleosidic monomers are linked by phosphodiester bonds. Whenever an oligonucleotide is represented by a sequence of letters, such as "ATGAGTCATGCG, it will be understood that the nucleotides are in 5' to 3' order from left to right and that "A" denotes deoxyadenosine, "C" denotes deoxycytidine, "G" denotes deoxyguanosine, "T" denotes deoxythymidine, and "U" denotes the ribonucleotide, uridine, unless otherwise noted. Usually oligonucleotides comprise the four natural deoxynucleotides; however, they may also comprise ribonucleotides or non-natural nucleotide analogs. It is clear to those skilled in the art when oligonucleotides having natural or non-natural nucleotides may be employed in methods and processes described herein. For example, where processing by an enzyme is called for, usually oligonucleotides consisting solely of natural nucleotides are required. Likewise, where an enzyme has specific oligonucleotide or polynucleotide substrate requirements for activity, e.g., single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al., Molecular Cloning, Second Edition (Cold Spring Harbor Laboratory, New York, 1989), and like references. Oligo nucleotides and polynucleotides may be single stranded or double stranded.

Nucleic acid molecules may optionally include one or more non-standard nucleotide(s), nucleotide analog(s) and/or modified nucleotides. Examples of modified nucleotides include, but are not limited to diaminopurine, ST, 5-fluorouracil, 5-bromouracil, 5-chlorouracil, 5-iodouracil, hypoxanthine, Xantine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methyl-aminomethyluracil, 5-methoxyaminomethyl-2-thiouracil, beta-D-mannosylqueosine, 5'-methoxycarboxymethyluracil, 5-methoxyuracil, 2-methylthio-D46-isopentenyladenine, uracil-5-oxyacetic acid (v), Wybutoxosine, pseudouracil, queosine, 2-thiocytosine, 5-methyl-2-thiouracil, 2-thiouracil, 4-thiouracil, 5-methyluracil, uracil-5-oxyacetic acidmethylester, uracil-5-oxyacetic acid (v), 5-methyl-2-thiouracil, 3-(3-amino-3-N-2-carboxypropyl) uracil, (acp3)w, 2.6-diaminopurine and the like. Nucleic acid molecules may also be modified at the base moiety (e.g., at one or more atoms that typically are available to form a hydrogen bond with a complementary nucleotide and/or at one or more atoms that are not typically capable of forming a hydrogen bond with a complementary nucleotide), sugar moiety or phosphate backbone.

The terms "nucleotide analog," "altered nucleotide" and "modified nucleotide" refer to a non-standard nucleotide, including non-naturally occurring ribonucleotides or deoxyribonucleotides. In certain exemplary embodiments, nucleotide analogs are modified at any position so as to alter certain chemical properties of the nucleotide yet retain the ability of the nucleotide analog to perform its intended function. Examples of positions of the nucleotide which may be derivitized include the 5 position, e.g., 5-(2-amino) propyluridine, 5-bromo uridine, 5-propyne uridine, 5-propenyl uridine, etc.; the 6 position, e.g., 6-(2-amino) propyl uridine; the 8-position for adenosine and/or guanosines, e.g., 8-bromo guanosine, 8-chloro guanosine, 8-fluoroguanosine, etc. Nucleotide analogs also include deaza nucleotides, e.g., 7-deaza-adenosine; O- and N-modified (e.g., alkylated, e.g., N6-methyl adenosine, or as otherwise known in the art) nucleotides; and other heterocyclically modified nucleotide analogs such as those described in Herdewijn, Antisense Nucleic Acid Drug Dev., 2000 Aug. 10(4):297-310.

Nucleotide analogs may also comprise modifications to the Sugar portion of the nucleotides. For example the 2 OH-group may be replaced by a group selected from H, OR, R, F, Cl, Br, I, SH, SR, NH, NHR, NR, COOR, or OR, wherein R is substituted or unsubstituted C—C alkyl, alkenyl, alkynyl, aryl, etc. Other possible modifications include those described in U.S. Pat. Nos. 5,858,988, and 6,291,438.

The phosphate group of the nucleotide may also be modified, e.g., by substituting one or more of the oxygens of the phosphate group with sulfur (e.g., phosphorothioates), or by making other substitutions which allow the nucleotide to perform its intended function such as described in, for example, Eckstein, Antisense Nucleic Acid Drug Dev. 2000 Apr. 10(2): 117-21, Rusckowski et al. Antisense Nucleic Acid Drug Dev. 2000 Oct. 10(5):333-45, Stein, Antisense Nucleic Acid Drug Dev. 2001 Oct. 11(5):317-25, Vorobjevet al. Antisense Nucleic Acid Drug Dev. 2001 Apr. 11(2): 77-85, and U.S. Pat. No. 5,684,143. Certain of the above referenced modifications (e.g., phosphate group modifications) decrease the rate of hydrolysis of for example, polynucleotides comprising said analogs in vivo or in vitro.

Nucleic acid molecules may be isolated from natural sources or purchased from commercial Sources. Oligonucleotide sequences may also be prepared by any suitable method, e.g., standard phosphoramidite methods such as those described by Beaucage and Carruthers (1981) Tetrahedron Lett. 22: 1859) or the triester method according to Matteucci et al. (1981). J. Am. Chem. Soc. 103:3185), or by other chemical methods using either a commercial automated oligonucleotide synthesizer or high-throughput, high density array methods known in the art (see U.S. Pat. Nos. 5,602,244, 5,574,146, 5,554,744, 5,428,148, 5,264,566, 5,141,813, 5,959,463, 4,861,571 and 4,659,774, incorporated herein by reference in its entirety for all purposes). Pre-synthesized oligonucleotides may also be obtained commercially from a variety of vendors.

In certain embodiments, nucleic acid sequences expressed in, derived from or obtained from one or more organisms or host cells are provided. As used herein, the term "organism" includes, but is not limited to, a human, a non-human primate, a cow, a horse, a sheep, a goat, a pig, a dog, a cat, a rabbit, a mouse, a rat, a gerbil, a frog, a toad, a fish (e.g., *Danio rerio*) a roundworm (e.g., *C. elegans*) and any transgenic species thereof. As used herein, a "host cell" can be any cell derived or obtained from an organism. The terms "organism" and "host cell" further include, but are not limited to, a yeast (e.g., *S. cerevisiae*) cell, a yeast tetrad, a yeast colony, a bacterium, a bacterial colony, a virion, Virosome, virus-like particle and/or cultures thereof, and the like.

In certain aspects of the invention, vectors and plasmids useful for transformation of a variety of host cells are provided. Vectors and plasmids are common and commercially available from companies such as Invitrogen Corp.

(Carlsbad, Calif.), Stratagene (La Jolla, Calif.), New England Biolabs, Inc. (Beverly, Mass.) and Addgene (Cambridge, Mass.).

Certain aspects of the invention pertain to vectors, Such as, for example, expression vectors. As used herein, the term "vector" refers to a nucleic acid sequence capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. By way of example, but not of limitation, a vector of the invention can be a single-copy or multi-copy vector, including, but not limited to, a BAC (bacterial artificial chromosome), a fosmid, a cosmid, a plasmid, a Suicide plasmid, a shuttle vector, a P1 vector, an episome, YAC (yeast artificial chromosome), a bacteriophage or viral genome, or any other suitable vector. The host cells can be any cells, including prokaryotic or eukaryotic cells, in which the vector is able to replicate.

Certain vectors are capable of autonomous replication in a host cell into which they are introduced (e.g., bacterial vectors having a bacterial origin of replication and episomal mammalian vectors). Other vectors (e.g., non episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors."

In general, expression vectors of utility in recombinant DNA techniques are often in the form of plasmids. In the present specification, "plasmid" and "vector can be used interchangeably. However, the invention is intended to include Such other forms of expression vectors, such as viral vectors (e.g., replication defective retroviruses, adenoviruses and adeno-associated viruses), which serve equivalent functions.

In certain exemplary embodiments, an exogenous nucleic acid described herein is expressed in bacterial cells using a bacterial expression vector Such as, e.g., a fosmid. A fosmid is a cloning vector that is based on the bacterial F-plasmid. The host bacteria will typically only contain one fosmid molecule, although an inducible high-copy on can be included such that a higher copy number can be obtained (e.g., pCC1FOSTM, pCC2FOSTM). Fosmid libraries are particularly useful for constructing stable libraries from complex genomes. Fosmids and fosmid library production kits are commercially available (EPICENTRER Biotechnologies, Madison, Wis.). For other suitable expression systems US 2016/0369248 A1 for both prokaryotic and eukaryotic cells see chapters 16 and 17 of Sambrook, J., Fritsh, E. F., and Maniatis, T. Molecular Cloning. A Laboratory Manual. 2nd, ed., Cold Spring Harbor Laboratory, Cold Spring Harbor Laboratory Press, Cold Spring Harbor, N.Y., 1989.

In certain exemplary embodiments, the recombinant expression vectors comprise a nucleic acid sequence in a form Suitable for expression of the nucleic acid sequence in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the foreign nucleic acid sequence encoding a plurality of ribonucleic acid sequences described herein is linked to the regulatory sequence(s) in a manner which allows for expression of the nucleic acid sequence. The term "regulatory sequence" is intended to include promoters, enhancers and other expression control elements (e.g., polyadenylation signals). Such regulatory sequences are described, for example, in Goeddel; Gene Expression Technology. Methods in Enzymology 185, Academic Press, San Diego, Calif. (1990). It will be appreciated by those skilled in the art that the design of the expression vector can depend on Such factors as the choice of the host cell to be transformed, the level of expression of protein desired, and the like.

Another aspect of the invention pertains to host cells into which a recombinant expression vector of the invention has been introduced. The terms "host cell" and "recombinant host cell are used interchangeably herein. It is understood that such terms refer not only to the particular Subject cell but to the progeny or potential progeny of such a cell. Because certain modifications may occur in Succeeding generations due to either mutation or environmental influences, such progeny may not, in fact, be identical to the parent cell, but are still included within the scope of the term as used herein.

Cells according to the present disclosure include any cell into which foreign nucleic acids can be introduced and expressed as described herein. It is to be understood that the basic concepts of the present disclosure described herein are not limited by cell type. Cells according to the present disclosure include eukaryotic cells, prokaryotic cells, animal cells, plant cells, insect cells, fungal cells, archaeal cells, eubacterial cells, a virion, a viroSome, a virus-like particle, a parasitic microbe, an infectious protein and the like. Cells include eukaryotic cells such as yeast cells, plant cells, and animal cells. Particular cells include bacterial cells. Other suitable cells are known to those skilled in the art.

Foreign nucleic acids (i.e., those which are not part of a cell's natural nucleic acid composition) may be introduced into a cell using any method known to those skilled in the art for such introduction. Such methods include transfection, transduction, infection (e.g., viral transduction), injection, microinjection, gene gun, nucleofection, nanoparticle bombardment, transformation, conjugation, by application of the nucleic acid in a gel, oil, or cream, by electroporation, using lipid-based transfection reagents, or by any other suitable transfection method. One of skill in the art will readily understand and adapt Such methods using readily identifiable literature sources.

As used herein, the terms "transformation' and" transfection' are intended to refer to a variety of art recognized techniques for introducing foreign nucleic acid into a host cell, including calcium phosphate or calcium chloride co-precipitation, DEAE-dextran-mediated transfection, lipofection (e.g., using commercially available reagents such as, for example, LIPOFECTIN® (Invitrogen Corp., San Diego, Calif.), LIPOFECTAMINE® (Invitrogen), FUGENER) (Roche Applied Science, Basel, Switzerland), JETPEI™ (Polyplus-transfection Inc., New York, N.Y.), EFFECT-ENE®) (Qiagen, Valencia, Calif.), DREAM FECT™ (OZ Biosciences, France) and the like), or electroporation (e.g., in vivo electroporation). Suitable methods for transforming or transfecting host cells can be found in Sambrook, et al. (Molecular Cloning: A Laboratory Manual. 2nd, ed., Cold Spring harbor Laboratory, Cold Spring Harbor Laboratory Press, Cold Spring Harbor, N.Y., 1989), and other laboratory manuals.

Initiation control regions or promoters, which are useful to drive expression of the relevant pathway coding regions in the desired host cell are numerous and familiar to those skilled in the art. Virtually any promoter capable of driving these genetic elements is suitable for the present invention including, but not limited to, lac, ara, tet, trp, IP, IP, T7, tac, and trc (useful for expression in *Escherichia coli* and *Pseudomonas*); the amy, apr, npr promoters and various phage promoters useful for expression in *Bacillus subtilis*, and *Bacillus licheniformis*; nis A (useful for expression in gram positive bacteria, Eichenbaum et al. Appl. Environ. Microbiol. 64(8):2763-2769 (1998)); and the synthetic P11 promoter (useful for expression in *Lactobacillus plantarum*, Rud et al., Microbiology 152: 1011-1019 (2006)). Termination control regions may also be derived from various genes native to the preferred hosts.

Vectors useful for the transformation of *E. coli* are common and commercially available. For example, the desired genes may be isolated from various sources, cloned onto a modified puC19 vector and transformed into *E. coli* host cells. Alternatively, the genes encoding a desired biosynthetic pathway may be divided into multiple operons, cloned into expression vectors, and transformed into various *E. coli* Strains.

According to certain aspect of the invention, phages and their genetic material are provided. As used herein, the terms "phage" and "bacteriophage" are used interchangeably. Phage can be distinguished from each another based on their genetic composition and/or their virion morphology. Some phages have double stranded DNA genomes, including phage of the corticoviridae, lipothrixviridae, plasmaviridae, myroVridae, siphoviridae, Sulfolobus shibate, podoviridae, tectiviridae and fuselloviridae families. Other phages have single Stranded DNA genomes, including phage of the microviridae and inoviridae families. Other phages have RNA genomes, including phage of the leviviridae and cystoviridae families. Exemplary bacterio phage include, but are not limited to, Wphi, Mu, T1, T2, T3, T4, T5, T6, T7, P1, P2, P4, P22, fa, phié, phi29, phiC31, phi80, phiX174, SP01, M13, MS2, PM2, SSV-1, L5, PRD1, Qbeta, lambda, UC-1, HK97, HK022 and the like.

Isolation, extraction or derivation of nucleic acid sequences may be carried out by any suitable method. Isolating nucleic acid sequences from a biological sample generally includes treating a biological sample in Such a manner that nucleic acid sequences present in the sample are extracted and made available for analysis. Any isolation method that results in extracted nucleic acid sequences may be used in the practice of the present invention. It will be understood that the particular method used to extract nucleic acid sequences will depend on the nature of the source.

Methods of DNA extraction are well-known in the art. A classical DNA isolation protocol is based on extraction using organic solvents such as a mixture of phenol and chloroform, followed by precipitation with ethanol (J. Sam brook et al., "Molecular Cloning: A Laboratory Manual." 1989, 2" Ed., Cold Spring Harbour Laboratory Press: New York, N.Y.). Other methods include: salting out DNA extraction (P. Sunnucks et al., Genetics, 1996, 144: 747-756; S. M. Aljanabi and I. Martinez, Nucl. Acids Res. 1997, 25: 46924693), trimethylammonium bromide salts DNA extraction (S. Gustincich et al., BioTechniques, 1991, 11:298-302) and guanidinium thiocyanate DNA extraction (J. B. W. Hammond et al., Biochemistry, 1996, 240: 298-300). A variety of kits are commercially available for extracting DNA from biological samples (e.g., BD Biosciences Clontech (Palo Alto, Calif.): Epicentre Technologies (Madison, Wis.); Gentra Systems, Inc. (Minneapolis, Minn.); MicroProbe Corp. (Bothell, Wash.); Organon Teknika (Durham, N.C.); and Qiagen Inc. (Valencia, Calif.)).

Methods of RNA extraction are also well known in the art (see, for example, J. Sambrook et al., "Molecular Cloning: A Laboratory Manual" 1989, 2" Ed., Cold Spring Harbour Laboratory Press: New York) and several kits for RNA extraction from bodily fluids are commercially available (e.g., Ambion, Inc. (Austin, Tex.): Amersham BioSciences (Piscataway, N.J.); BD Biosciences Clontech (Palo Alto, Calif.); BioRad Laboratories (Hercules, Calif.); Dynal Biotech Inc. (Lake Success, N.Y.); Epicentre Technologies (Madison, Wis.); Gentra Systems, Inc. (Minneapolis, Minn.); GIBCO BRL (Gaithersburg, Md.); Invitrogen Life Technologies (Carlsbad, Calif.); MicroProbe Corp. (Bothell, Wash.); Organon Teknika (Durham, N.C.); Promega, Inc. (Madison, Wis.); and Qiagen Inc. (Valencia, Calif)).

Certain embodiments of the subject invention are directed to a first nucleic acid (e.g., a nucleic acid sequence encoding a VSW-3 RNAP) or polypeptide sequence (e.g., a VSW-3 RNAP) having a certain sequence identity or percent homology to a second nucleic acid or polypeptide sequence, respectively.

Techniques for determining nucleic acid and amino acid "sequence identity" are known in the art. Typically, such techniques include determining the nucleotide sequence of genomic DNA, mRNA or cDNA made from an mRNA for a gene and/or determining the amino acid sequence that it encodes, and comparing one or both of these sequences to a second nucleotide or amino acid sequence, as appropriate. In general, "identity" refers to an exact nucleotide-to-nucleotide or amino acid-to-amino acid correspondence of two polynucleotides or polypeptide sequences, respectively. Two or more sequences (polynucleotide or amino acid) can be compared by determining their "percent identity." The percent identity of two sequences, whether nucleic acid or amino acid sequences, is the number of exact matches between two aligned sequences divided by the length of the shorter sequences and multiplied by 100.

An approximate alignment for nucleic acid sequences is provided by the local homology algorithm of Smith and Waterman, Advances in Applied Mathematics 2:482-489 (1981). This algorithm can be applied to amino acid sequences by using the scoring matrix developed by Dayhoff, Atlas of Protein Sequences and Structure, M. O. Dayhoff ed., 5 suppl. 3:353-358, National Biomedical Research Foundation, Washington, D.C., USA, and normalized by Gribskov (1986) Nucl. Acids Res. 14:6745. An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.).

One method of establishing percent identity in the context of the present invention is to use the MPSRCH package of programs copyrighted by the University of Edinburgh, developed by John F. Collins and Shane S. Sturrok, and distributed by IntelliGenetics, Inc. (Mountain View, Calif.). From this suite of packages, the Smith Waterman algorithm can be employed where default parameters are used for the scoring table (for example, gap open penalty of 12, gap extension penalty of one, and a gap of six). From the data generated the "match value reflects" sequence identity." Other Suitable programs for calculating the percent identity or similarity between sequences are generally known in the art, for example, another alignment program is BLAST, used with default parameters. For example, BLASTN and BLASTP can be used using the following default parameters: genetic code-standard; filter-none; strand=both; cut-off=60, expect=10; Matrix=BLOSUM62: Descriptions=50 sequences; sort by=HIGH SCORE; Databases-non-redundant, GenBank EMBL-DDBJ-PDB+GenBank CDS translations—Swiss US 2016/0369248 A1 protein-Spupdate-PIR. Details of these programs can be found at the NCBI/NLM web site.

In certain exemplary embodiments, a polymerase of the subject invention (e.g., a VSW-3 RNAP) includes one or more protein tags. As used herein, the term "protein tag" refers to a heterologous polypeptide sequence linked to a polymerase of the invention. Protein tags include, but are not limited to, His tag (HHHHHH) (SEQ ID NO: 13), calmodulin tag (KRRWKKNFIAVSAANRFKKISSSGAL) (SEQ ID NO:14), FLAG tag (DYKDDDDK) (SEQ ID NO:15), HA tag (YPYDVPDYA) (SEQ ID NO:16), Avi tag (GLN-DIFEAQKIEWHE) (SEQ ID NO:17), Myc tag (EQKLI-SEEDL) (SEQ ID NO:18), S tag (KETAAAKFERQHMDS) (SEQ ID NO:19), SBP tag (MDEKTTGWRGGHVVEG-LAGELEQLRARLEHHPQGQREP) (SEQ ID NO:20), Softag 1 (SLAELLNAGLGGS) (SEQ ID NO:21), Softag 3 (TQDPSRVG) (SEQ ID NO:22), V5 tag (GKPIPN-PLLGLDST) (SEQ ID NO:23), Xpress tag (DLYDDDDK) (SEQID NO: 24), Isopeptag (TDKDMTITFTNKKDAE) (SEQ ID NO: 25), SpyTag (AHIVMVDAYKPTK) (SEQID NO:26), and streptactin tag (Strep-tag II: WSHPOFEK) (SEQ ID NO:27).

As used herein, a "kit" refers to any delivery system for delivering materials or reagents for carrying out a method of the invention. In the context of assays, such delivery systems include systems that allow for the storage, transport, or delivery of reaction reagents (e.g., enzymes (e.g., a polymerase such as, for example, VSW-3 RNAP), nucleotides, buffers, etc. in the appropriate containers) and/or supporting materials (e.g., written instructions for performing the assay (e.g., in vitro transcription), etc.) from one location to another. For example, kits include one or more enclosures (e.g., boxes) containing the relevant reaction reagents and/or Supporting materials for assays of the invention. Such contents may be delivered to the US 2016/0369248 A1 intended recipient together or separately. For example, a first container may contain an enzyme (e.g., enzymes (e.g., a polymerase Such as, for example, phage VSW-3 RNAP)) for use in an assay, while a second container contains nucleotides.

The present disclosure relates to methods of purifying *Pseudomonas* phage VSW-3 RNAP, methods of expressing VSW-3 RNAP, applications of purified VSW-3 RNAP, and in vitro transcription systems utilizing novel promoter sequences and VSW-3 RNAP.

The RNA polymerase (RNAP) of VSW-3 is homologous to T7 RNAP based on DNA sequence, although it is somewhat smaller in size. Characterization of the VSW-3 RNAP is particularly interesting since its host, *Pseudomonas fluorescens* SW-3, is one of the classic psychrophilic bacteria and therefore may have new features that provide insight into the low-temperature activity of transcription systems. An important step in understanding the transcription of the VSW-3 genome is the establishment of a transcription system in vitro. Furthermore, the VSW-3 RNAP possesses properties that distinguish it from T7 RNAP since it is adapted to the plateau wetlands' cold environment.

A single subunit DNA-dependent RNAP was identified and purified to apparent homogeneity from phage VSW-3 that infects the *Pseudomonas fluorescens*. VSW-3 is homologous to bacteriophage T7 that infects *E. coli*. The DNA encoding a VSW-3 RNAP has least about 95% sequence identity to the nucleic acid sequence set forth as SEQ ID NO: 9. The VSW-3 RNAP may have a protein tag (such as SEQ ID NO: 13). In some embodiments, the protein tag is a His tag.

In some embodiments, the VSW-3 RNAP comprises an amino acid sequence of SEQ ID NO: 5. It is known in the art that the introduction of one or more amino acid substitutions to a protein sometimes may not seriously affect certain function (e.g., RNA polymerase activity) of the protein, such as conservative substitutions. Therefore, some variants of the VSW-3 RNAP, which retain the RNA polymerase activity, are also envisaged. In some embodiments, the VSW-3 RNAP has at least about 80%, at least about 85%, at least about 90%, at least about 95%, at least about 98%, at least about 99%, or even 100% sequence identity to the amino sequence of SEQ ID NO: 5. In some embodiments, the VSW-3 RNAP variant comprises a Y578F mutation when compared with SEQ ID NO: 5. As will be described below, this VSW-3 RNAP variant is able to efficiently utilize some modified nucleotides (e.g., 2'-F-dATP and/or 2'-F-dUTP) to produce mRNA or other transcripts. The amino acid sequence of the VSW-3 RNAP variant is set forth in SEQ ID NO: 6.

The VSW-3 RNAP can be expressed in a host cell by introducing an expression vector carrying a DNA fragment encoding the VSW-3 RNAP into the host cell and culturing the host cell under suitable conditions. In some embodiments, the DNA fragment encoding the VSW-3 RNAP comprises the nucleotide sequence of SEQ ID NO: 9. Since codon degeneracy is well known in the art, other DNA fragment encoding the same VSW-3 RNAP are also possible. Accordingly, in some embodiments, the DNA fragment encoding the VSW-3 RNAP may has at least about 80% (e.g., at least about 85%, at least about 90%, at least about 95%, at least about 98%, at least about 99%, or even 100%) sequence identity to the nucleotide sequence of SEQ ID NO: 9.

In certain exemplary embodiments, a method of purifying VSW-3 RNAP is provided. The method includes the steps of expressing a VSW-3 RNA polymerase comprising a heterologous protein tag at 10° C., and purifying the VSW-3 RNAP by contacting chromatography columns.

In some embodiments, the purified VSW-3 RNAP may include a heterologous polypeptide sequence, e.g., a protein tag, selected from the group consisting of one or any combination of Avi tag, calmodulin tag, FLAG tag, HA tag, proS2 tag, His tag, Myc tag, S tag, SBP tag, Sof ag 1, Softag 3, V5 tag, Xpress tag, Isopep tag, Spy Tag, biotin carboxyl carrier protein tag, glutathione-stranferase tag, green fluorescent protein tag, maltose binding protein tag, NuS tag, streptavidin tag, Streptactin tag, and thioredoxin tag. In some embodiments, the protein tag is removable from the purified VSW-3 RNAP.

Figure 2:
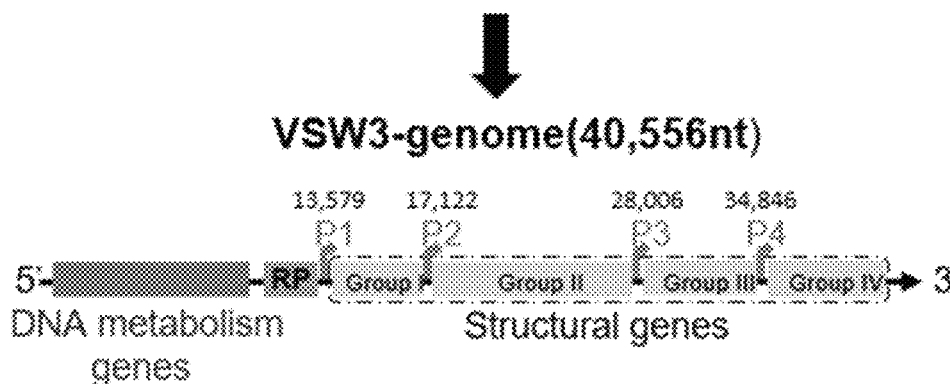
FIG. 2. The promoter predicted for VSW-3 RNAP and the positions in the VSW-3 genome.

The promoter has been identified by examining transcription of pUC19-DNA template with predicted 21 nt long promoter (5'-TTAATTGGGCCACCTATAGTA-3' (SEQ ID NO: 38)) of VSW-3 RNAP and sequencing the 5'-termini of the transcripts confirmed 5'-TTAATTGGGCCACCTATA-3' (SEQ ID NO: 1) are necessary, which appears four times within the VSW-3 genome (FIG. 2). The first promoter is located right behind the VSW-3 RNAP gene and the other three are distributed in the intergenic sequence of genome. The purified enzyme and its promoter have enabled a determination of the requirements for transcription reaction.

The enzyme predominantly used for in vitro run-off RNA synthesis is bacteriophage T7 RNAP. However, T7 RNAP mostly synthesizes run-off products with the products having non-based additional nucleotides (3'+N tails). This contaminating products are extremely difficult to remove and impede the function of these RNAs in applications where a precise 3'-terminus of the RNA is critical. However, the single subunit RNAP from phage VSW-3 produces precise run-off transcripts without non-specific extension in their 3'-end and makes it advantageous for production of RNAs that require precise 3'-terminus such as sgRNA, RNA probes, RNA primers.

Since 37° C. is the optimal enzyme activity temperature for T7 RNAP, and most nuclease activities are also extremely high at this temperature, if a small amount of nuclease contamination during the process of transcription reaction, it will cause severe degradation of the transcription products. However, if the temperature is lowered to 25° C., the nuclease activity will be significantly reduced. Under the premise of the same amount of nuclease contamination, even if the transcription reaction time is increased from 1 hour to 24 hours, the amount of degradation of the transcription product is also significantly reduced. Coincidentally, VSW3 RNAP requires 25° C. for maximal activity to synthesize RNA products, it can effectively reduce the risk of RNA products degradation.

Accordingly, in certain exemplary embodiments, a method of performing in vitro transcription is provided. The method includes the steps of providing a DNA containing a VSW-3 RNAP promoter sequence and a nucleic acid template sequence, a VSW-3 RNAP enzyme, and nucleotides, and incubating the nucleic acid template sequence, the VSW-3 RNAP and nucleotides together for a sufficient time to produce transcripts.

In some embodiments, the transcripts are selected from the group consisting of one or any combination of mRNA, tRNA, rRNA, miRNA, siRNA, snRNA, snoRNA, ribozymes, aptamers and RNA fragments. The incubation step is performed in different concentration of $MgCl_2$ and DTT, at a concentration of $MgCl_2$ at 0 mM, 1 mM, 2 mM, 3 mM, 4 mM, 5 mM, 6 mM, 7 mM, 8 mM, 9 mM, 10 mM, 11 mM, 12 mM, 14 mM, 16 mM, 18 mM and 20 mM, then at a concentration of DTT at 0 mM, 1 mM, 2 mM, 3 mM, 4 mM, 5 mM, 6 mM, 7 mM, 8 mM, 9 mM, 10 mM, 11 mM, 12 mM, 14 mM, 16 mM, 18 mM and 20 mM. The incubation step is performed at 4° C., 10° C., 15° C., 20° C., 25° C., 30° C. or 37° C., and incubating time is 1 h, 2 h, 4 h, 6 h, 8 h, 10 h, 12 h, 14 h, 16 h, 18 h, 20 h, 24 h or 36 h.

In some embodiments, the nucleic acid template sequence comprises class II terminators sequence (5'-ATCTGTT-3') and full-length transcripts can be synthesized without any interrupt products by VSW-3 RNAP.

In certain exemplary embodiments, a kit for in vitro transcription is provided. The kit includes a DNA plasmid comprising one or more promoter sequences, each promoter sequence having the nucleic acid sequence set forth as SEQ ID NO:1, wherein the one or more promoter sequences provide transcriptional control of an operably linked polynucleotide sequence, a VSW-3 RNAP (such as an isolated VSW-3 RNAP or a purified VSW-3 RNAP, or a synthetic VSW-3 RNAP), 5× Transcription Buffer, optional nucleotides substrates, and instructions for use. In certain embodiments, the VSW-3 RNAP includes a protein tag. In other embodiments, the operably linked polynucleotide sequence comprises one or more restriction sites.

In certain exemplary embodiments, a method of producing single-stranded RNA (ssRNA) transcripts without double-stranded RNA (dsRNA) contamination is provided. The method includes the steps of providing a template sequence encoding the polynucleotide sequence and a VSW-3 promoter sequence, contacting the template sequence with VSW-3 RNAP and allowing the VSW-3 RNAP to bind the VSW-3 RNAP promoter sequence and produce dsRNA-free transcripts.

This invention is further illustrated by the following examples, which should not be construed as limiting. The contents of all references, patents and published patent applications cited throughout this application are hereby incorporated by reference in their entirety for all purposes.

EXAMPLES

Example 1

Materials and Methods

Oligonucleotides were obtained from GeneCreate company. DNA purification kits were from Axygen and Ni-NTA resin was from Qiagen. Preparative Superdex 5200 for gel filtration was from GE Healthcare. Gibson assembly kit, T4 RNA ligase II, rNTP, DNase I, Apyrase and T7 RNA polymerase (#M0251L) were from New England Biolabs. Reverse transcriptase kit (#6110A) and PrimeSTAR Max DNA Polymerase (#R045A) were from TaKaRa. RNA Clean kit was from New England Biolabs. RiboLock RNase Inhibitor (#E00382) was from Thermo Scientific™. Recombinant inorganic pyrophosphatase (PPA) expressed by *Escherichia coli* (#15907) was from Sigma-Aldrich. 5-methylcytidine 5'-triphosphate, pseudouridine-5'-triphosphate and 5moU were from Trilink.

Example 2

Protein Purification

Genomic DNA sequence of phage VSW-3 was first released online by the Gene Bank (KX066068.1). DNA fragments encoding VSW-3 RNAP were synthesized by GeneCreat company, and were inserted into plasmid pCold vector (TaKaRa) between the NdeI and NotI sites. Plasmids were transformed into *E. coli* BL21 (DE3). The bacteria were cultured in 1 L LB medium containing 50 g/mL Amp+ at 30° C. until they reached an OD600 of approximately 0.8. The bacterial cultures were placed the on ice for 10 min and then the expression of VSW-3 RNAP was induced by the addition of 0.2 mM IPTG at 10° C. After an additional incubation of 24 hr, cells were harvested, resuspended in 50 mM Tris-HCl, pH 7.5 and 100 mM NaCl, and lysed by three cycles of freeze-thaw in the presence of 0.5 mg/mL lysozyme. Clear lysate was collected by centrifugation at 15000 rpm and loaded onto the 2.5 mL Ni+ resin, the resin was then washed with 50 mL of wash buffer (Tris-HCl, pH 7.5, 100 M NaCl, and 20 mM imidazole). VSW-3 RNAP was eluted from the column with 80 mL elution buffer containing 50 mM Tris-HCl, pH 7.5, 100 mM NaCl and 20 to 100 mM imidazole gradient, fractions were analyzed on SDS-PAGE gels, a pool of the fractions containing predominately RNAP was concentrated by Amicon Ultra-15 Centrifugal Filter and further purified by gel filtration chromatography on a 200 mL preparative Superdex 5200 column. Fractions from gel filtration chromatography were analyzed on SDS-PAGE gels and those containing pure RNAP were pooled and concentrated by Amicon Ultra-15 Centrifugal Filter, then dialyzed against 50 mM Tris-HCl (pH 7.5), 100 mM NaCl, 1 mM DTT, 0.1 mM EDTA, 0.1% Triton X-100 and 50% glycerol, and stored at –20° C. The fractions from each chromatography step with highest VSW-3 RNAP purity were shown in FIG. 1. The concentration of VSW-3

RNAP has been measured with Bradford method. In SDS-PAGE gel. SDS-PAGE gel of purified 6×His-tagged VSW-3 RNAP were stained with Comassie Blue.

Example 3

DNA Templates

DNA templates for in vitro transcription assays were described in the present Example. PCR reactions were carried out using PrimeSTAR Max DNA Polymerase (TaKaRa). PCR products were purified using PCR products Extraction Kits (Axygen) and DNA concentrations were measured by UV spectrophotometer (Nano-drop).

Figure 3:
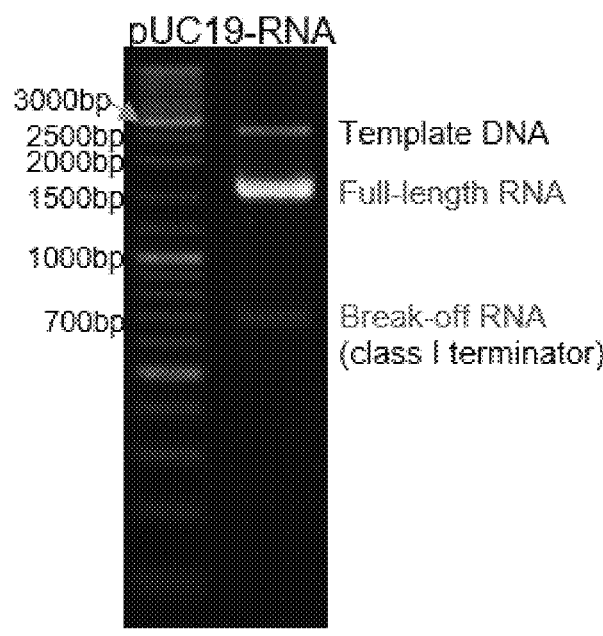
FIG. 3. Insert the predicted promoter sequence (5'-TTAATTGGGCCACCTATAGTA-3' (SEQ ID NO: 38)) into pUC19 plasmid between BamH I and XbaI, the constructed plasmid pUC19-VSW3p was linearized by NdeI and transcribed with 10× transcription buffer from T7 RNAP's (New England Biolabs), the transcription reaction was carried out at 20° C. over night. The electrophoresis results of the transcripts were showed in this figure.

DNA templates for transcription assays were either linearized plasmids, PCR products or dsDNA fragments of annealed complementary oligonucleotides. First, the predicted promoter "TTAATTGGGCCACCTATAGTA (SEQ ID NO: 38)" of VSW-3 RNAP was inserted between the BamH I and Xba 1 sites of plasmid pUC19 to form pUC19-VSW3p, which was then linearized with Nde I restriction enzyme to serve as the template to determine the activity of purified VSW-3 RNAP (FIG. 3). The transcription was carried out with 10× transcription buffer from T7 RNAP's (New England Biolabs) at 20° C. over night.

The transcription templates for determining the exact 5'-end sequence of VSW-3 RNAP promoter were constructed by annealing two complementary synthetic DNA oligos as following (F: plus strand; R: minus strand):

```
VSW3-promoter Test (18)-F:
                              (SEQ ID NO: 28)
TTAATTGGGCCACCTATAGTACACGGGCA

GCTTGCCGGGTTTTAGAGCTAGAAATAGC

VSW3-promoter Test(18)-R:
                              (SEQ ID NO: 29)
GCTATTTCTAGCTCTAAAACCCGGCAAGC

TGCCCGTGTACTATAGGTGGCCCAATTAA

VSW3-promoter Test(17)-F:
                              (SEQ ID NO: 30)
TAATTGGGCCACCTATAGTACACGGGCAG

CTTGCCGGGTTTTAGAGCTAGAAATAGC

VSW3-promoter Test(17)-R:
                              (SEQ ID NO: 31)
GCTATTTCTAGCTCTAAAACCCGGCAAGC

TGCCCGTGTACTATAGGTGGCCCAATTA

VSW3-promoter Test(16)-F:
                              (SEQ ID NO: 32)
AATTGGGCCACCTATAGTACACGGGCAGC

TTGCCGGGTTTTAGAGCTAGAAATAGC

VSW3-promoter Test(16)-R:
                              (SEQ ID NO: 33)
GCTATTTCTAGCTCTAAAACCCGGCAAGC

TGCCCGTGTACTATAGGTGGCCCAATT

VSW3-promoter Test(15)-F:
                              (SEQ ID NO: 34)
ATTGGGCCACCTATAGTACACGGGCAGCT

TGCCGGGTTTTAGAGCTAGAAATAGC

VSW3-promoter Test(15)-R:
                              (SEQ ID NO: 35)
GCTATTTCTAGCTCTAAAACCCGGCAAGC
```

-continued

```
TGCCCGTGTACTATAGGTGGCCCAAT

VSW3-promoter Test(14)-F:
                         (SEQ ID NO: 36)
TTGGGCCACCTATAGTACACGGGCAGCTT

GCCGGGTTTTAGAGCTAGAAATAGC

VSW3-promoter Test(14)-R:
                         (SEQ ID NO: 37)
GCTATTTCTAGCTCTAAAACCCGGCAAGC

TGCCCGTGTACTATAGGTGGCCCAA
```

All templates were the same except for the 5'-end one by one nucleotide shortening from the 18 nt promoter to 14 nt, as indicated in parentheses.

Figure 16:
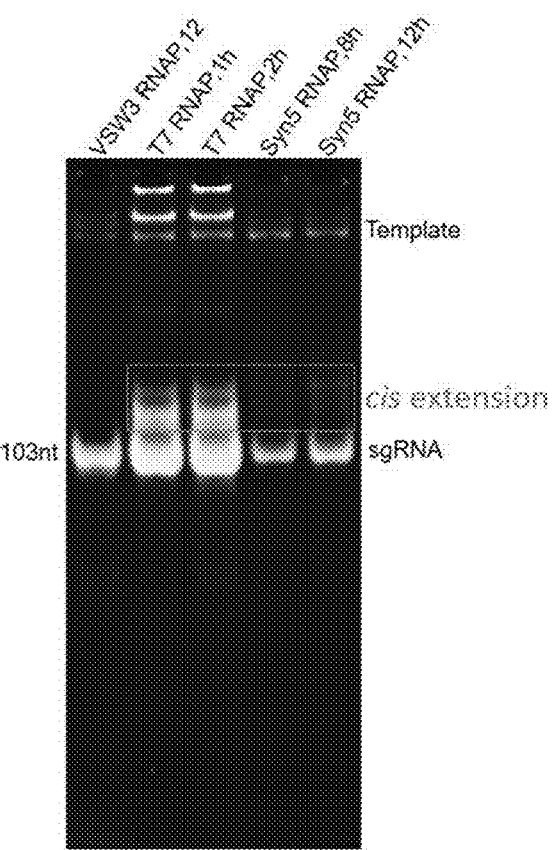
FIG. 16. According to the 12% TBE native PAGE gel of synthesized sgRNA (targeting at eGFP) with T7, VSW-3 and Syn5 RNAP, for unknown reasons, like T7 and Syn5 RNAP, some break-off sgRNA products are synthesized by VSW-3 RNAP, but only the VSW-3 RNAP do not present the non-specifically extended RNA products from the gel.

Three plasmids modified based on pUC19 (pUC19-VSW3p-sgRNA, pUC19-T7p-sgRNA and pUC19-Syn5p-sgRNA), each harbors the same sgRNA coding sequence (targeting eGFP) under the control of VSW-3 promoter, T7 promoter, and Syn5 promoter, respectively, were constructed, linearized by BspQ1 treatment, and recovered by DNA extraction kit (Axgen) to serve as templates for FIG. 16. According to the 12% TBE native PAGE gel of synthesized sgRNA (targeting at eGFP) with T7, VSW-3 or syn5 RNAP, for unknown reasons, like T7 and Syn5 RNAP, some break-off sgRNA products are synthesized by VSW-3 RNAP, but only the VSW-3 RNAP do not present the non-specifically extended RNA products from the gel.

The plasmid (cas9-T7p) containing cas9 coding sequence under the control of T7 RNAP promoter was from addgene (#72247). Another plasmid (cas9-VSW3p) was modified based on cas9-T7p, of which the T7 promoter was replaced by a VSW-3 promoter. The transcription templates for cas9 RNA by T7 RNAP or VSW-3 RNAP were PCR amplified from cas9-T7p or cas9-VSW3p using primers (Trans_Template-cas9-F AGCTGGTTTAGTGAACCGTCAGATC (SEQ ID NO: 39) and Trans_Template-cas9-R: ACT-CAATGGTGATGGTGATGATGACC (SEQ ID NO: 40)), respectively.

Example 4

Transcription Assays

Initially, the transcription buffer containing 40 mM Tris-HCl (pH7.9), 6 mM MgCl$_2$, 2 mM spermidine, and 1 mM DTT as described in T7 RNAP transcription kit (New England Biolabs) was used in the transcription assays for VSW-3 RNAP's activity confirmation and promoter determination. For gel assays shown in FIG. 3, reaction mixtures (10 ul) contained 40 mM Tris-HCl (pH7.9), 6 mM MgCl$_2$, 2 mM spermidine, 1 mM DTT, 0.5 mM ATP, 0.5 mM CTP, 0.5 mM GTP, 0.5 mM UTP, 0.5 U RNaseoOUT™ recombinant ribonuclease inhibitor (Invitrogen), 0.2 uM Recombinant inorganic pyrophosphatase, 0.15 uM VSW-3 and 30 ng/ul of linearized pUC19-VSW3p plasmid, reaction mixtures were incubated at 20° C. for 12 h. Reactions were then terminated by the addition of 2× loading dye containing 95% formamide, 40 mM EDTA, 0.02% (w/v) SDS, 0.05% (w/v) Bromophenol Blue and 0.05% (w/v) Xylene Cyanol. Samples were then heated at 85° C. for 2 min and loaded onto 1.5% native TAE-Agarose gels. After electrophoresis, gels were stained with Ethidium bromide (EB) and analyzed using a UV gel imager.

Figure 4:
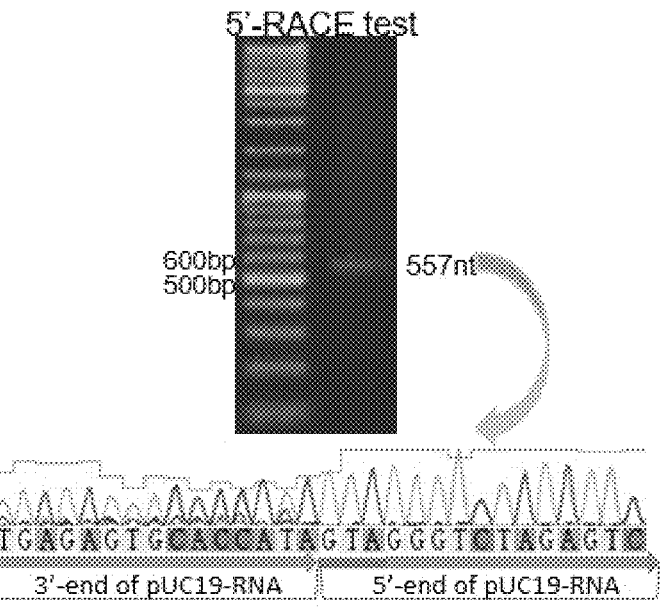
FIG. 4. 5'-RACE to confirm the accurate nucleotides on the 3'-end of VSW-3 RNAP promoter.
Figure 5:
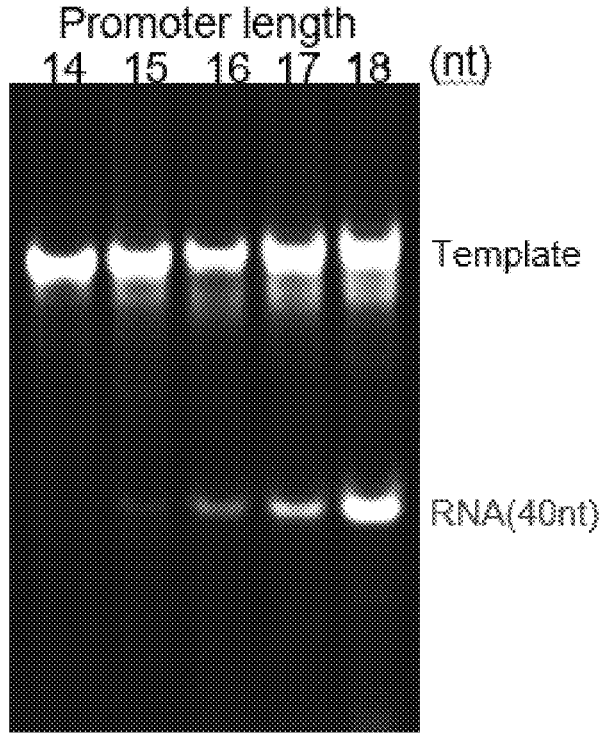
FIG. 5. For confirmation of the accurate nucleotides on the 5'-end of VSW-3 RNAP promoter. Synthesis of a short DNA transcription template as truncated promoter on the 5'-end. Transcription reaction results show that 15 nt is the shortest and necessary length of promoter (5'-ATTGGGC-CACCTATA-3' (SEQ ID NO: 4)) for VSW-3 RNAP, but the 18 nt long promoter (5'-TTAATTGGGCCACCTATA-3' (SEQ ID NO: 1)) will be needed to synthesize much more products.

To determine the 5' boundary of VSW-3 RNAP promoter, the reaction mixtures for FIG. 5 contained 40 mM Tris-HCl (pH7.9), 6 mM MgCl$_2$, 2 mM spermidine, 1 mM DTT, 0.5 mM ATP, 0.5 mM CTP, 0.5 mM GTP, 0.5 mM UTP, 0.5 U RNaseoOUT™ recombinant ribonuclease inhibitor (Invitrogen), 0.2 uM Recombinant inorganic pyrophosphatase, 0.15 μM VSW-3 RNAP and 4 μM of annealed complementary oligos VSW3-promoter Test (18)-F/R, VSW3-promoter Test (17)-F/R, VSW3-promoter Test (16)-F/R, VSW3-promoter Test (15)-F/R, or VSW3-promoter Test (14)-F/R, of which the sequences were described in Example 3. Reaction mixtures were incubated at 20° C. for 12 h. Reactions were then terminated by the addition of 2×RNA loading dye. Samples were then heated at 85° C. for 2 min and loaded onto 12% native TBE-PAGE gels. After electrophoresis, gels were stained with Ethidium bromide (EB) and analyzed using a UV gel imager. The transcription reaction results showed that 15 nt (5'-ATTGGGCCACCTATA-3' (SEQ ID NO: 4)) was the shortest and necessary length of promoter, but the 18 nt long promoter (5'-TTAATTGGGCCACC-TATA-3' (SEQ ID NO: 1)) will be needed to synthesize much more products. In addition, we confirmed that the transcription start nucleotide was "GTA" through 5'-RACE (FIG. 4).

Figure 6:
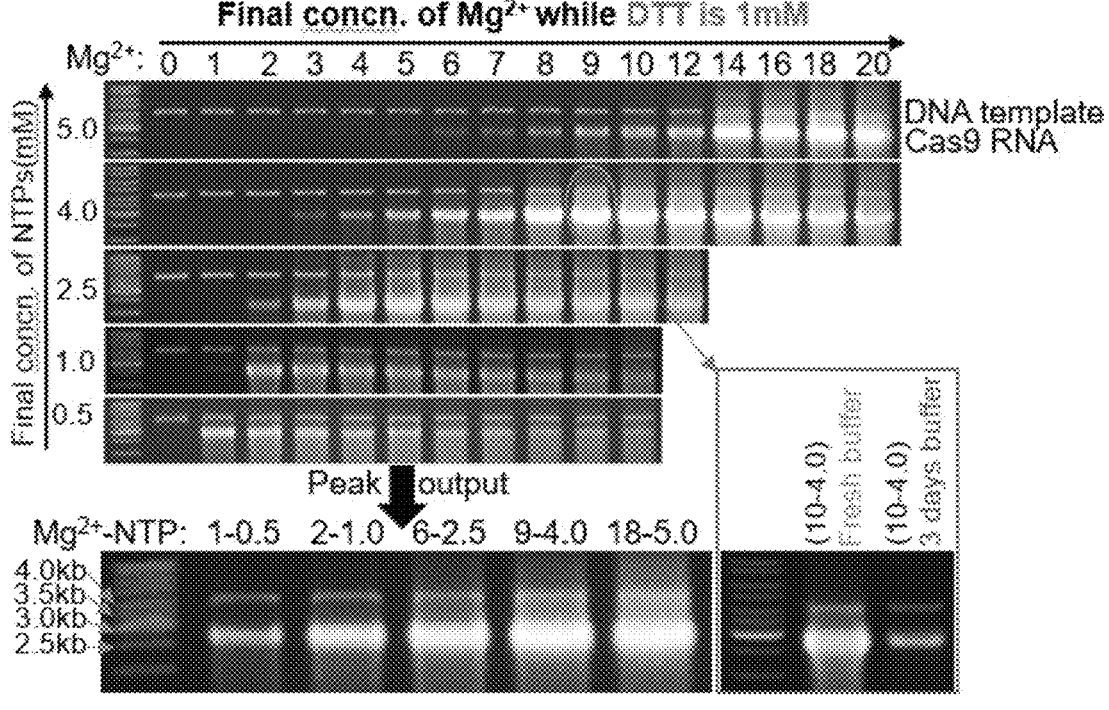
FIG. 6. Screening for suitable transcriptional conditions for VSW-3 RNAP. (A) Screening for the best concentration of Mg$^{2+}$ (0 mM, 1 mM, 2 mM, 3 mM, 4 mM, 5 mM, 6 mM, 7 mM, 8 mM, 9 mM, 10 mM, 12 mM, 14 mM, 16 mM, 18 mM, 20 mM) with 1 mM DTT in the transcription buffer by adding different concentrations of NTP (0.5 mM, 1 mM, 2.5 mM, 4 mM, 5 mM). At last, we found that the buffer formula of 9 mM Mg$^{2+}$, 1 mM DTT and 4 mM NTP facilitates the synthesis of considerable amounts of RNA, but it is not a stable transcriptional buffer for VSW-3 RNAP.

To optimize the VSW-3 RNAP reaction condition, we first screened the concentration of Mg$^{2+}$ (0 mM, 1 mM, 2 mM, 3 mM, 4 mM, 5 mM, 6 mM, 7 mM, 8 mM, 9 mM, 10 mM, 12 mM, 14 mM, 16 mM, 18 mM, 20 mM) in combination with 1 mM DTT and various concentrations of NTPs (0.5 mM, 1 mM, 2.5 mM, 4 mM, 5 mM) in FIG. 6. Then three high concentrations of DTT (5 mM and 20 mM) were also tested to establish a stable and high-yield transcription buffer with a final NTP concentration of 4 mM. At last, we found that the buffer formula of 9 mM Mg2+, 1 mM DTT and 4 mM NTP facilitates the synthesis of considerable amounts of RNA, but it was not a stable transcriptional buffer for VSW-3 RNAP.

Figure 7:
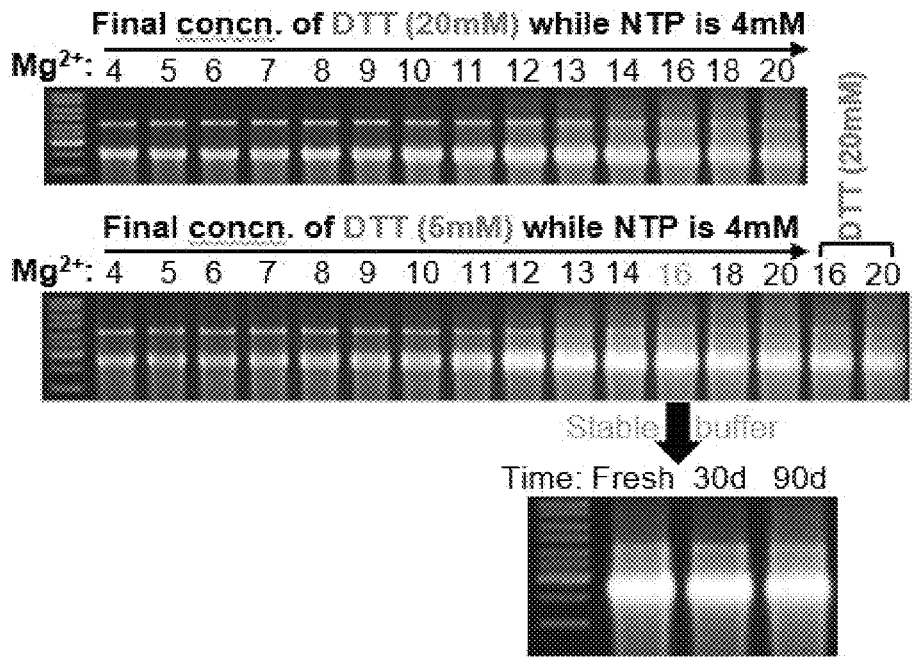
FIG. 7. Screen for a stable and high-yield transcription buffer contains 5 mM and 20 mM of DTT (final concentration) while the final concentration of Mg$^{2+}$ increasing from 4 mM to 20 mM while the NTP is 4 mM. A stable and high-yield buffer of 16 mM Mg$^{2+}$, 5 mM DTT with 4 mM NTP was found for VSW-3 RNAP.

For the assays described in FIG. 7, reaction mixtures (10 μL) contained 40 mM Tris-HCl (pH 8.0), 16 mM MgCl$_2$, 2 mM spermidine, 5 mM DTT, 4 mM NTPs, 30 ng/ul transcription template of cas9 RNA as described above in Example 3, 0.5 U RNaseoOUT™ recombinant ribonuclease inhibitor (Invitrogen), 0.2 uM recombinant inorganic pyrophosphatase, and 0.15 uM VSW-3 RNAP. All reaction mixtures were incubated at 20° C. for 12 hours and reactions were then terminated by the addition of 2× loading dye as described above. Samples were then heated at 85° C. for 2 min and placed on ice for 2 min, then loaded onto 1.5% native TAE-Agarose gels. After electrophoresis, gels were stained with Ethidium bromide (EB) and analyzed using a UV gel imager. A stable and high-yield buffer of 16 mM Mg$^{2+}$, 5 mM DTT with 4 mM NTP was found for VSW-3 RNAP.

Figure 8:
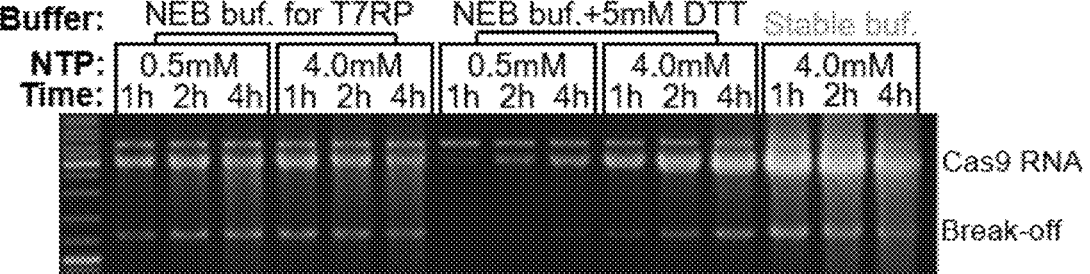
FIG. 8. Different from the 10× transcription buffer as introduced in the T7 RNAP instruction (New England Biolabs), the stable and high-yield transcription buffer of VSW-3 RNAP is also efficient for T7 RNAP to obtain the high yield of RNA products in 1 hour.

To test the effect of the optimized VSW-3 RNAP transcription buffer on T7 RNAP (FIG. 8), either optimized T7 or VSW-3 buffer was used for T7 RNAP to transcribe the cas9 gene on PCR-amplified transcription template containing T7 promoter. All assays contained 0.5 mM or 4 mM each NTPs and (1) T7 RNAP 10× transcription buffer (New England Biolabs) with additional 5 mM fresh DTT; or (2) The optimized VSW-3 buffer mentioned above containing 40 mM Tris-HCl (pH 8.0), 16 mM MgCl$_2$, 5 mM DTT, and 2 mM spermidine. After incubation the reaction mixture was mixed directly with denaturing loading buffer and loaded onto 1.5% TAE agarose gel, electrophoresis for 30 minutes at 100 V, then the gel was stained with ethidium bromide (EB) and analyzed using a UV gel imager. The results were shown in FIG. 8. Different from the 10× transcription buffer as introduced in the T7 RNAP instruction (New England Biolabs), the stable and high-yield transcription buffer of VSW-3 RNAP is also efficient for T7 RNAP to obtain the high yield of RNA products in 1 hour.

Figure 9:
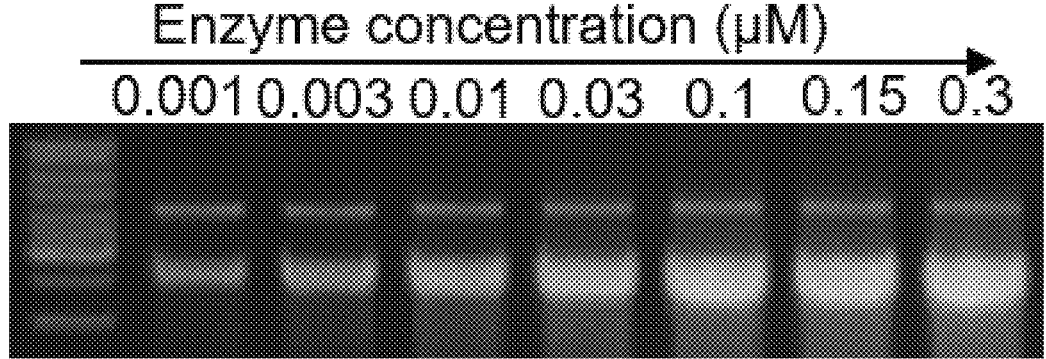
FIG. 9. The final enzyme concentration of VSW-3 RNAP reached to 0.15 μM, the yield of RNA reach its peak.

According to results above, the optimal reaction temperature for VSW-3 RNAP is 25, then the reactions as in FIG. 9 were carried out to determine the optimal concentration of VSW-3 RNAP. Reaction mixtures (10 µL) contained stable transcription buffer (40 mM Tris-HCl (pH8.0), 16 mM MgCl₂, 5 mM DTT, 2 mM spermidine), and 4 mM NTPs, 0.5 U RNaseoOUT™ recombinant ribonuclease inhibitor (Invitrogen), 0.2 uM recombinant inorganic pyrophos-phatase, 30 ng/ul transcription template of cas9 gene, and various concentration of VSW-3 RNA-P: 0.001 µM, 0.003 µM, 0.01 µM, 0.03 µM, 0.1 µM, 0.2 µM and 0.4 µM at 25° C. for 12 h. Reaction was terminated by the addition of 2× loading dye, heated at 85° C. for 2 min and placed on ice for 2 min, then loaded onto 1.5% native TAE-Agarose gels. After electrophoresis, gels were stained with Ethidium bromide (EB) and analyzed using a UV gel imager. When the final enzyme concentration of VSW-3 RNAP reached to 0.15 µM, the yield of RNA reached its peak.

Figure 10:
FIG. 10. The optimum reaction temperature for VSW-3 RNAP is 25° C.
Figure 10:
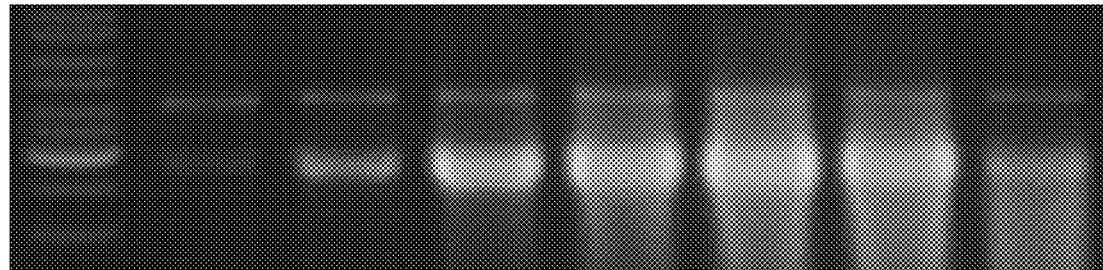

According to the steps above, the stable transcription buffer for VSW-3 RNAP was established, then the reactions for FIG. 10 were carried out to determine the optimal temperature for maximal RNA yield by VSW-3 RNAP. Each of the reaction mixtures (10 ul) contained stable transcrip-tion buffer (40 mM Tris-HCl (pH8.0), 16 mM MgCl₂, 5 mM DTT, 2 mM spermidine), 4 mM NTPs, 0.5 U RNaseoOUT™ recombinant ribonuclease inhibitor (Invitrogen), 0.2 uM recombinant inorganic pyrophosphatase, 0.15 uM VSW-3 RNAP and 30 ng/ul transcription template of cas9 gene, reaction mixtures were incubated at various temperature (4° C., 10° C., 15° C., 20° C., 25° C., 30° C., 37° C.) for 12 h. Reactions were then terminated by the addition of 2× loading dye. Samples were then heated at 85° C. for 2 min and placed on ice for 2 min, then loaded onto 1.5% native TAE-Agarose gels. After electrophoresis, gels were stained with Ethidium bromide (EB) and analyzed using a UV gel imager. The optimum reaction temperature for VSW-3 RNAP was 25° C.

Figure 11:
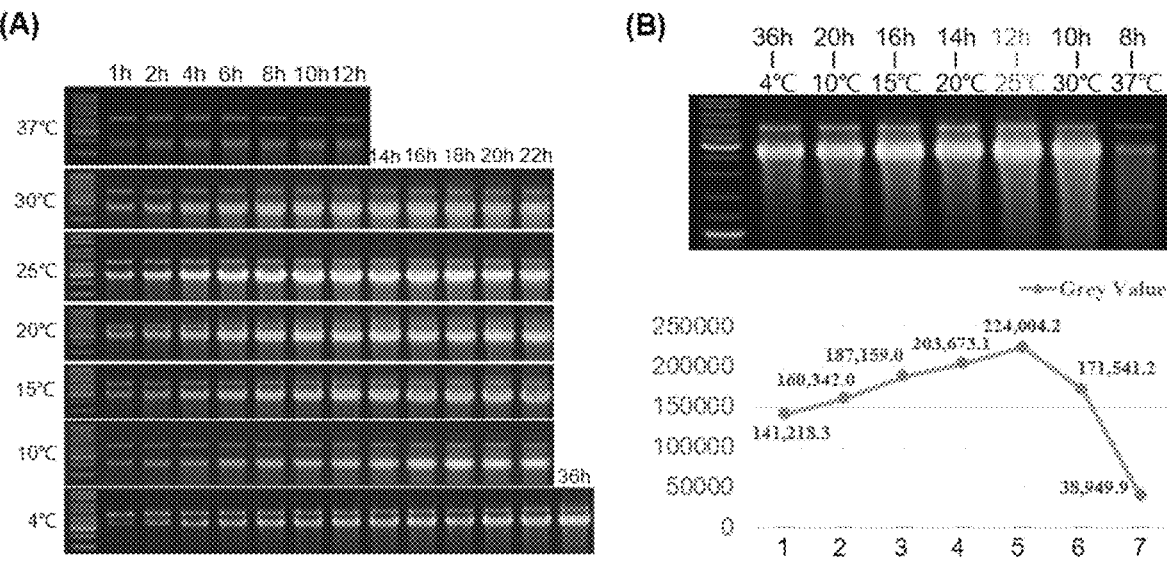
FIG. 11. (A) Collected the reaction mixture every two hours at temperatures (4° C., 10° C., 15° C., 20° C., 25° C., 30° C., 37° C.) to find out the time needed at different temperatures for VSW-3 RNAP. (B) The maximal yield of RNA products obtained at 25° C., required for 12 hours.

In order to determine the reaction time for VSW-3 RNAP to obtain the highest yield of RNA at various temperatures, each of reaction mixtures (20 µL) contained 40 mM Tris-HCl (pH8.0), 16 mM MgCl₂, 5 mM DTT, 2 mM spermidine, 4 mM each of 4 NTPs, 0.5 U RNaseoOUT™ recombinant ribonuclease inhibitor (Invitrogen), 0.2 µM recombinant inorganic pyrophosphatase, 0.15 µM VSW-3 RNAP and 30 ng/µL transcription template of cas9 gene (FIG. 11A). 4 µL reaction mixture was taken every two hours at different temperatures, and mixed with 4 µL, of 2× loading dye. Samples were then heated at 85° C. for 2 min and placed on ice for 2 min, then loaded onto 1.5% native TAE-Agarose gels. After electrophoresis, gels were stained with Ethidium bromide (EB) and analyzed using a UV gel imager. Samples corresponding to the highest RNA yield at each temperature was analyzed on 1.5% native TAE-Agarose gel (FIG. 11B). The maximal yield of RNA products were obtained at 25° C. after 12 hours.

Figure 12:
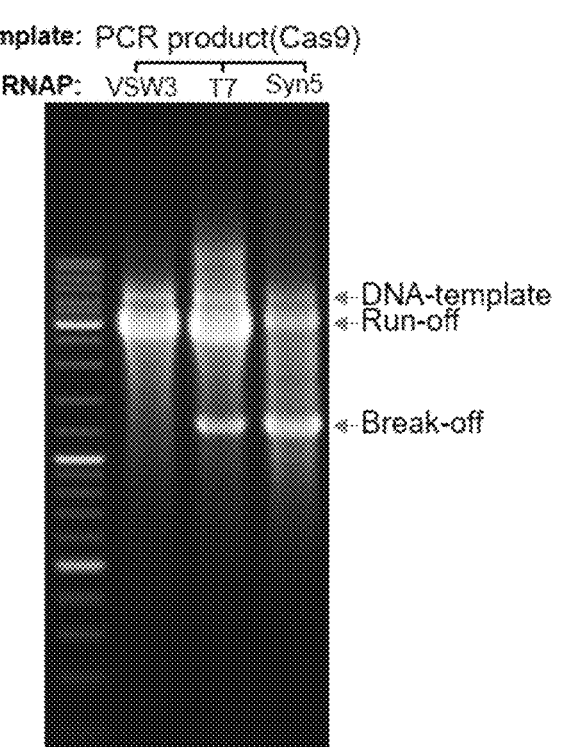
FIG. 12. The cas9-RNA was transcribed by T7, VSW-3 and Syn5 RNAP while the transcription templates were prepared by PCR. Both T7 RNAP and Syn5 RNAP got a break-off RNA products, but VSW-3 RNAP won't.
Figure 13:
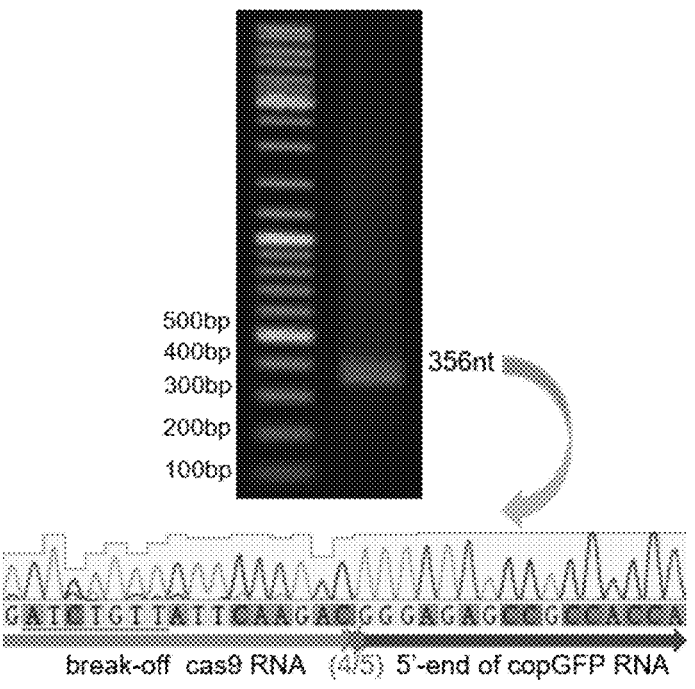
FIG. 13. 3'-RACE was carried out to verify the break-off site that T7 and Syn5 RNAP encountered while the transcription templates were prepared by PCR, found that there was a class II terminator "ATCTGTT" located just 9 nucleobases upstream from the break-off site.

During the optimization of transcription condition with PCR-amplified cas9 coding DNA as transcription template, we found that there is a group of smaller RNA products synthesized by T7 RNAP estimated to be 1500 nt-1600 nt long according to the marker in the Agarose gel (FIG. 12), but not in VSW-3 RNAP products. In order to characterize these undesired T7 products, 3'-RACE was conducted. A 5' primer (5'-GTATTGCCTAAGCACAGTTTACT-3' (SEQ ID NO: 41)) was designed and the fragment containing the RNA 3' sequence information was amplified by PCR. Then the PCR product was inserted into pET28 plasmid between BamHI and EcoRI sites with Gibson Assembly Cloning method, plasmids were then amplified in E. coli DH5α cells and sent for Sanger sequencing (FIG. 13). 3'-RACE was carried out to verify the break-off site that T7 encountered while the transcription templates were prepared by PCR. It was found that there was a class II terminator "ATCTGTT" located just 9 nucleobases upstream from the break-off site.

Figure 14:
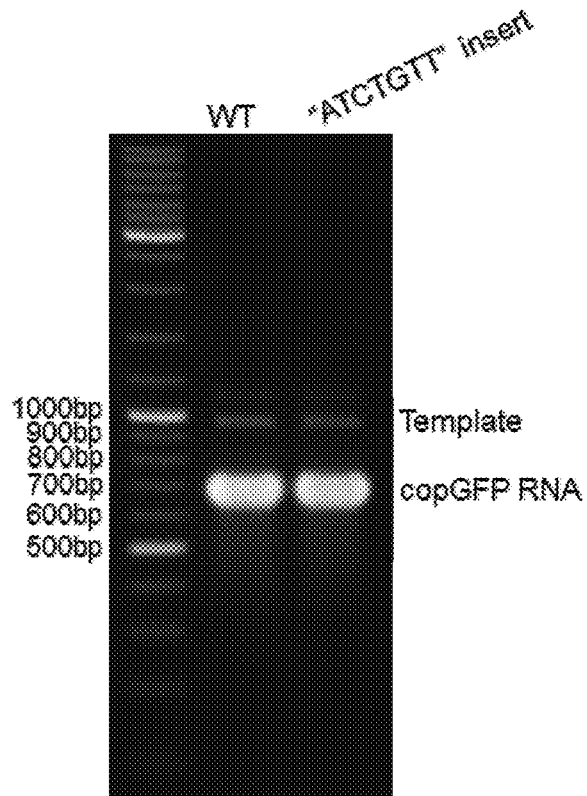
FIG. 14. The insertion of the class II terminator "ATCTGTT" into the copGFP gene verified that the VSW-3 RNAP is insensitive to the class II terminator and transcription will not be interrupted.

In order to investigate the effect of class II T7 terminator on VSW-3 RNAP transcription, the typical class II termi-nator sequence "ATCTGTT" was inserted into the copGFP gene located at the 433 nt from the 5-end. The transcription reactions were carried out as described above, the RNA product was assayed by native 1.5% agarose gel electro-phoresis (FIG. 14). The insertion of the class II terminator "ATCTGTT" into the copGFP gene verified that the VSW-3 RNAP is insensitive to the class II terminator and transcrip-tion will not be interrupted.

Figure 15:
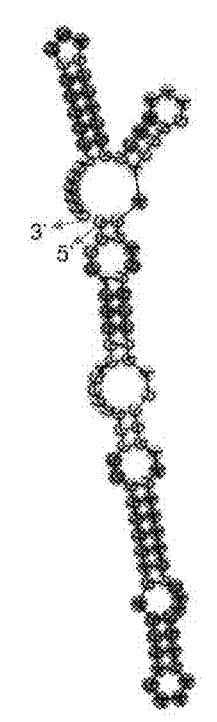
FIG. 15. The secondary structure of sgRNA targeted eGFP (GenBank: MT277585.1) was predicted with RNAfold software.

In order to examine the RNA extension by T7 and VSW-3 RNAP on RNA with terminal secondary structure, we used both RNAPs to synthesize an sgRNA (its coding sequence: 5'-GGGCACGGGCAGCTTGCCGGGTTT-TAGAGCTAGAAATAGCAAGTTAAAATAAG GCTAGTCCGTTATCAACTT-GAAAAAGTGGCACCGAGTCGGTGCTTTTTTT-3' (SEQ ID NO: 7) targeting eGFP gene (FIG. 15). First, we prepared the DNA fragments encoding the above sgRNA sequence with the T7 or VSW-3 promoter sequence attached on their 5'-ends, respectively, and inserted either fragment into pUC19 plasmid between BamHI and XhoI restriction endonuclease sites. After amplification of the constructed plasmids, we designed a pair of universal amplification primers (sgRNA template-F: 5'-ATCAGGCGCCATTCGC-CATTCAGG-3' (SEQ ID NO: 42), sgRNA template-R: 5'-AAAAAAAGCACCGACTCGGTGCCACT-3' (SEQ ID NO: 43)) to prepare the transcription templates for sgRNAs by PCR. Here, we applied a final NTPs concentration of 4 mM and sgRNA transcription templates of 30 ng/µL, respec-tively. Reactions were then terminated by the addition of 2× loading dye. Samples were then heated at 85° C. for 2 min and placed on ice for 2 min, then loaded onto 12% native TBE-PAGE gels. After electrophoresis, gels were stained with Ethidium bromide (EB) and analyzed using a UV gel imager (FIG. 16). According to the 12% TBE native PAGE gel of synthesized sgRNA (targeting eGFP) with T7, VSW-3 and syn5 RNAP, for unknown reasons, like T7 and Syn5 RNAP, some break-off sgRNA products are synthesized by VSW-3 RNAP, but only the VSW-3 RNAP do not present the non-specifically extended RNA products from the gel.

Figure 17:
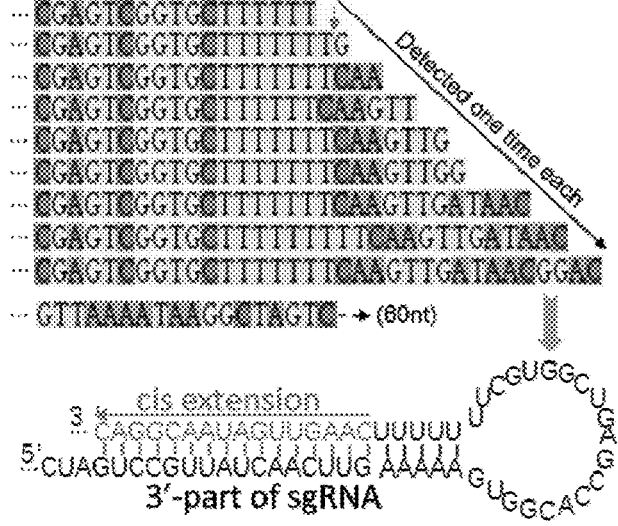
FIG. 17. 3'-RACE test for sgRNAs transcribed by T7 and VSW-3 RNAP reflected that T7 RNAP readily synthesizes a lot of extended RNA products, VSW-3 RNAP was prone to synthesize precise full-length sgRNA and some truncated sgRNA products. According to the sequencing results of 3-RACE for sgRNA synthesized by T7 RNAP, up to 16 nt were cis-extended at the 3'-end of sgRNA by T7 RNAP.

We carried out 3'-RACE test to detect the sgRNA product terminal homogeneity of T7 RNAP and VSW-3 RNAP by linking the mono-phosphorylated copGFP RNA to the 3'-end of the sgRNAs with RNA ligase II (New England Biolabs), then conducted the reverse transcription synthesis of cDNA as above and carried out PCR with primers (3RACE-sgRNA-F-sgRNA: 5'-GCAGCTTGCCGGGTTT-TAGAGCTAG-3' (SEQ ID NO: 44); 3RACE-sgRNA R-sgRNA: 5'-TAGCCCATCACGTGGCTCAGCA-3' (SEQ ID NO: 45)), the PCR products was checked by agarose gel electrophoresis. Then the purified PCR product was inserted into multiple cloning site of pET28 plasmid between BamH I and EcoR I with Gibson Assembly Cloning method, we picked 10 monoclonal colonies respectively for Sanger sequencing (FIG. 17). 3'-RACE test for sgRNAs transcribed by T7 or VSW-3 RNAP reflected that T7 RNAP readily synthesized a lot of undesirable extended RNA products, while VSW-3 RNAP was prone to synthesize precise full-length sgRNA and some truncated sgRNA products. According to the sequencing results of 3-RACE for sgRNA synthesized by T7 RNAP, up to 16 nt were cis-extended at the 3'-end of sgRNA by T7 RNAP.

Figure 18:
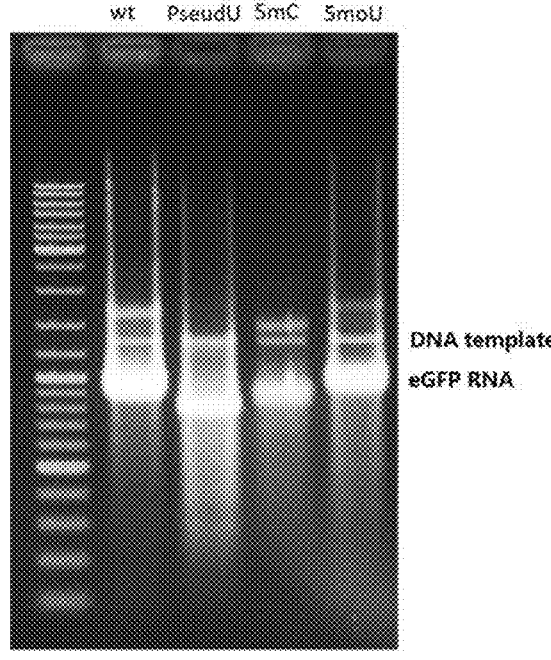
FIG. 18. The modified bases of 5mCTP, 5moUTP and pseudoUTP can be synthesized into mRNA by VSW-3 RNAP.

The capability of VSW-3 RNAP to incorporate pseudoUTP, 5mCTP and 5moUTP into RNA products was examined in the optimized VSW-3 reaction conditions mentioned above except that the UTP was replaced by pseudoUTP or 5moUTP, CTP was replaced by 5mCTP, respectively. Reactions were then terminated by the addition of 2× loading dye. Samples were then heated at 85° C. for 2 min and placed on ice for 2 min, then loaded onto 1.5% native TAE-Agarose gels. After electrophoresis, gels were stained with Ethidium bromide (EB) and analyzed using a UV gel imager (FIG. 18). The modified bases of 5mCTP, 5moUTP and pseudoUTP can be synthesized into mRNA by VSW-3 RNAP.

Figure 19:
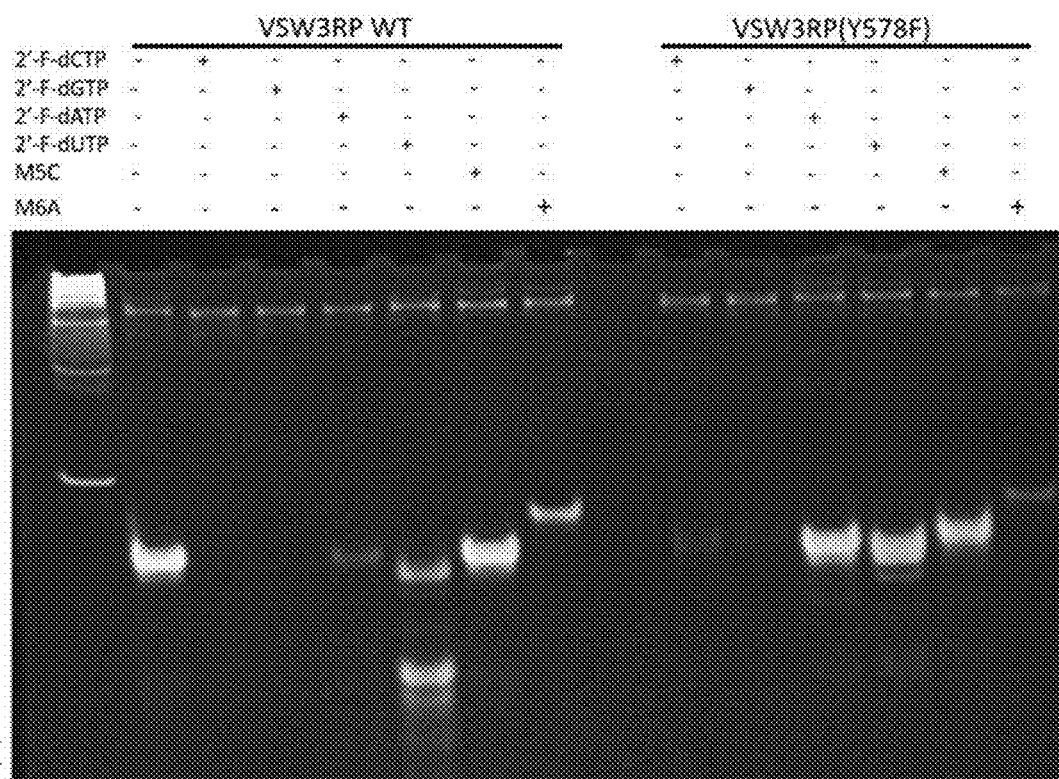
FIG. 19. With sgRNA as template, mutant VSW-3 RNAP (Y578F) had a strong ability to insert modified base 2'-F-deoxyribonucleotide when transcriptional RNA synthesis was performed. In particular, the efficiency of 2'-F-dATP and 2'-F-dUTP are significantly higher than that of wild-type VSW-3 RNAP, while the ability to insert m5CTP and m6ATP had no obvious difference.

Selected sgRNA transcription template described above was used to test if the VSW-3 RNAP Y578F mutant (SEQ ID NO: 6) had the advantage to incorporate 2-F-NTPs, 5mCTP and m6ATP. Reactions were the same optimized VSW-3 RNAP reaction conditions mentioned above except one of the 4 NTPs was replaced by its analog. Reactions were then terminated by the addition of 2× loading dye. Samples were then heated at 85° C. for 2 min and placed on ice for 2 min, then loaded onto 12% native TBE-PAGE gels. After electrophoresis, gels were stained with Ethidium bromide (EB) and analyzed using a UV gel imager (FIG. 19). With sgRNA as template, mutant VSW-3 RNAP (Y578F) had a strong ability to insert modified base 2'-F-deoxyribonucleotide when transcriptional RNA synthesis was performed. In particular, the efficiency of 2'-F-dATP and 2'-F-dUTP are significantly higher than that of wild-type VSW-3 RNAP, while the ability to insert m5CTP and m6ATP had no obvious difference.

Figure 20:
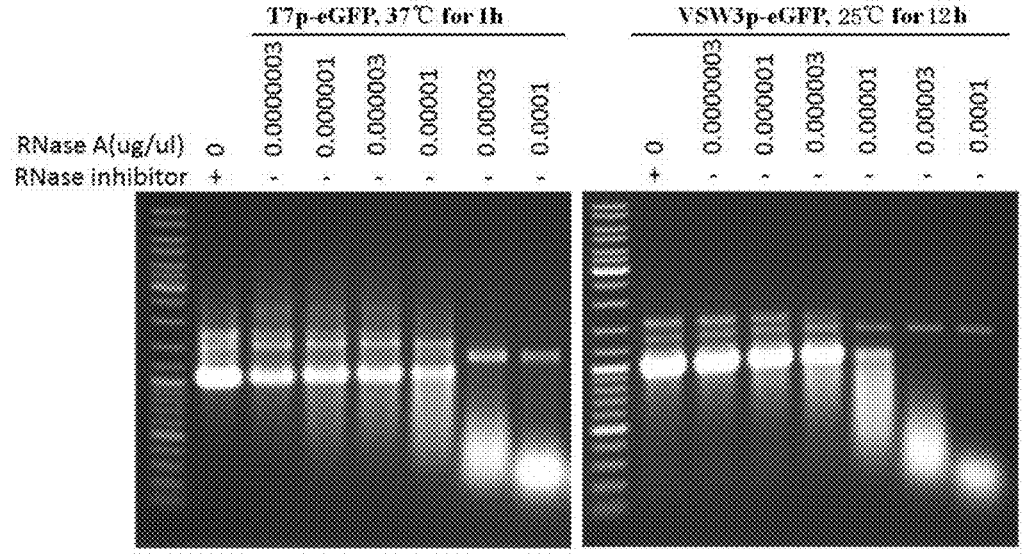
FIG. 20. Low temperature transcription synthesis RNA can significantly reduce the risk of degradation during RNA synthesis in vitro. Compared with T7 RNAP, the transcription of VSW-3 RNAP at its optimal transcription temperature (25) can resist more RNase A pollution. Even if the transcription time is longer, it will not cause more degradation.
Figure 21:
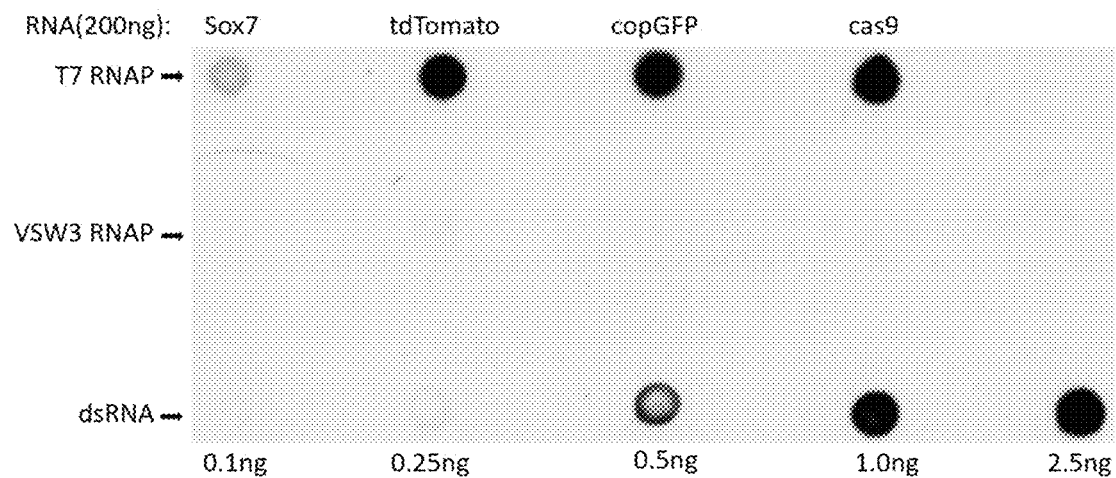
FIG. 21. Dot-blot test with the J2 monoclonal antibodies (mAbs) for dsRNA in the IVT products of T7 RNAP and VSW-3 RNAP. All T7 products (Sox7, tdTomato, copGFP, and cas9 RNA) contain dsRNA contamination, while dsRNA in the RNA products synthesized by VSW-3 RNAP is not detectable.

In order to demonstrate the advantage of carrying out in vitro RNA synthesis at relatively low temperature, we compared the vulnerability of VSW-3 RNAP or T7 RNAP reaction to RNase A contamination at their optimal temperatures. RNase A (final concentration from $1.0×10^{-4}$ ng/ul to $3.0×10^{-7}$ ng/ul) was added into the transcription reaction mixture. For VSW-3 RNAP, the reaction was performed at 25° C. for 12 hours, and for T7 RNAP, 37° C. for 1 h. Reactions were terminated by the addition of 2× loading dye, then heated at 85° C. for 2 min and placed on ice for 2 min, then loaded onto 1.5% native TAE-Agarose gels. After electrophoresis, gels were stained with Ethidium bromide (EB) and analyzed using a UV gel imager (FIG. 20). Low temperature transcription synthesis RNA can significantly reduce the risk of degradation during RNA synthesis in vitro. Compared with T7 RNAP, the transcription of VSW-3 RNAP at its optimal transcription temperature (25) can resist more RNase A pollution. Even if the transcription time is extended, it will not cause more degradation.

We conducted dot-blot with J2 monoclonal antibody to test dsRNA contamination in the several RNA transcripts (sox7, tdTomato, copGFP and cas9) from T7 and VSW-3 IVT. Construction of template plasmids was based on cas9-T7p and cas9-VSW3p plasmids, the cas9 coding sequence of both plasmids were replaced by either sox7, tdTomato or copGFP gene coding sequence (SEQ ID NOs:10-12). The transcription templates for sox7 and tdTomato RNA by T7 RNAP or VSW-3 RNAP were linearized by BSPQ1, and copGFP transcription templates were prepared by PCR amplified with primers (Trans_Template-cas9-F: AGCTGGTTTAGTGAACCGTCAGATC (SEQ ID NO: 39) and Trans_Template-cas9-R: ACTCAATGGTGATGGTGATGATGACC (SEQ ID NO: 40)).

The produced RNA (200 ng) was blotted onto nitrocellulose membrane (Millipore), dried, blocked with 5% non-fat dried milk in TBS-T buffer (50 mM Tris-HCl, 150 mM NaCl, 0.05% Tween-20, pH 7.4), and incubated with dsRNA-specific mAb J2 or K1 (English & Scientific Consulting) for 30 min. Membranes were washed 2 times with TBS-T and reacted with HRP-conjugated donkey anti-mouse Ig (Jackson Immunology), washed two times and detected with ECL Western blot detection reagent (Pierce). Images were captured on an X film (Kodak) photosensitive development. dsRNA (0.1 ng, 0.25 ng, 0.5 ng, 0.1 ng, 2.5 ng) used as a quantitative marker was derived from sense and antisense strands synthesized of a UTR sequence by VSW-3 RNAP.

Listed below are some amino acid sequences and nucleic acid sequences mentioned herein.

```
promoter for VSW-3 RNAP
                                    SEQ ID NO: 1
TTAATTGGGCCACCTATA promoter for VSW-3 RNAP
                                    SEQ ID NO: 2
TAATTGGGCCACCTATA promoter for VSW-3 RNAP
                                    SEQ ID NO: 3
AATTGGGCCACCTATA promoter for VSW-3 RNAP
                                    SEQ ID NO: 4
ATTGGGCCACCTATA VSW-3 RNAP protein sequence-WT
                                    SEQ ID NO: 5
MNQIELEQEMIDGGRAKMFGSFNRNEEQGAAHNNP

YAAAVYRRFVQPLADQIDAYCGEVKRGVMAAGKAL

LRPHDPMVLAFMTVRMVMDTTLQSKDNAPTAVARA

LGQSIYGETLLAKFEQVEPDLYFTLVNDFERRMTK

SERHRLTVFKMQAEKNGVPLPVWSPEDKLAIGTIL

LYLARDVGLVEITEVRKGKKTVREYNMTPDVAGML

DNIKDFVAGASPMVLPCVVPPVPWTDANNGGYHTP

GMRRISPCCIRGRPRVEDLTDVPDIPLRALNILQS

RPWRINRMVLDAVDLVGQRFDVGEVLAQAELPKPK

SLLWLDDVPKEEMNPAQLAEFGAWKIEMREWYTEN

KSRGVQWGRYYEALRVARKFKDLPFWFVYQYDYRG

RAYANTRGVSPQGSDLQKALLMADVGVPIADERAK

FWFYTAGANRFGYDKATLAERYEWTVERSEMICAI

AADPVANRQWTEADNPFQFLAWCFEFAQYTAMPES

FLSRLALGQDGSCNGLQHFSAMLRDEVGGLATNLV

PSTTQQDIYRLVAVETTRLLQAMPHENCEFTLKWK

LHSLSRDLVKRSVMTLPYGSTRFSCADFIYTEYMA

KHKAPEFAKGDYQKAARWLSVPVWDAIGNVVVKAR

EAMAWLQNASDELIDAGIDEIYWRSPSGFMVRQRY

GKEEFVLVKTRLAGGVRIRPTIKLELEEPCKRRHR

NGIAPNFVHSHDAAHMHLLICAAEDHGLGHLAFIH
```

-continued

DDYGTTADGTETLHKLIRATFVAMYEQGCPLTAFR

DTYGITEDLPERGDLDLNLVHDSTYFFA

VSW-3 RNAP protein sequence-Y578F
                    SEQ ID NO: 6
MNQIELEQEMIDGGRAKMFGSFNRNEEQGAAHNNP

YAAAVYRRFVQPLADQIDAYCGEVKRGVMAAGKAL

LRPHDPMVLAFMTVRMVMDTTLQSKDNAPTAVARA

LGQSIYGETLLAKFEQVEPDLYFTLVNDFERRMTK

SERHRLTVFKMQAEKNGVPLPVWSPEDKLAIGTIL

LYLARDVGLVEITEVRKGKKTVREYNMTPDVAGML

DNIKDFVAGASPMVLPCVVPPVPWTDANNGGYHTP

GMRRISPCCIRGRPRVEDLTDVPDIPLRALNILQS

RPWRINRMVLDAVDLVGQRFDVGEVLAQAELPKPK

SLLWLDDVPKEEMNPAQLAEFGAWKIEMREWYTEN

KSRGVQWGRYYEALRVARKFKDLPFWFVYQYDYRG

RAYANTRGVSPQGSDLQKALLMADVGVPIADERAK

FWFYTAGANRFGYDKATLAERYEWTVERSEMICAI

AADPVANRQWTEADNPFQFLAWCFEFAQYTAMPES

FLSRLALGQDGSCNGLQHFSAMLRDEVGGLATNLV

PSTTQQDIYRLVAVETTRLLQAMPHENCEFTLKWK

LHSLSRDLVKRSVMTLPFGSTRFSCADFIYTEYMA

KHKAPEFAKGDYQKAARWLSVPVWDAIGNVVVKAR

EAMAWLQNASDELIDAGIDEIYWRSPSGFMVRQRY

GKEEFVLVKTRLAGGVRIRPTIKLELEEPCKRRHR

NGIAPNFVHSHDAAHMHLLICAAEDHGLGHLAFIH

DDYGTTADGTETLHKLIRATFVAMYEQGCPLTAFR

DTYGITEDLPERGDLDLNLVHDSTYFFA sgRNA coding sequence
                    SEQ ID NO: 7
GGGCACGGGCAGCTTGCCGGGTTTTAGAGCTAGAA

ATAGCAAGTTAAAATAAGGCTAGTCCGTTATCAAC

TTGAAAAAGTGGCACCGAGTCGGTGCTTTTTTT cas9 RNA coding sequence
                    SEQ ID NO: 8
GGGAGAGCCGCCACCATGGATAAAAAGTATTCTAT

TGGTTTAGACATCGGCACTAATTCCGTTGGATGGG

CTGTCATAACCGATGAATACAAAGTACCTTCAAAG

AAATTTAAGGTGTTGGGGAACACAGACCGTCATTC

GATTAAAAAGAATCTTATCGGTGCCCTCCTATTCG

ATAGTGGCGAAACGGCAGAGGCGACTCGCCTGAAA

CGAACCGCTCGGAGAAGGTATACACGTCGCAAGAA

CCGAATATGTTACTTACAAGAAATTTTTAGCAATG

AGATGGCCAAAGTTGACGATTCTTTCTTTCACCGT

TTGGAAGAGTCCTTCCTTGTCGAAGAGGACAAGAA

-continued

ACATGAACGGCACCCCATCTTTGGAAACATAGTAG

ATGAGGTGGCATATCATGAAAAGTACCCAACGATT

TATCACCTCAGAAAAAAGCTAGTTGACTCAACTGA

TAAAGCGGACCTGAGGTTAATCTACTTGGCTCTTG

CCCATATGATAAAGTTCCGTGGGCACTTTCTCATT

GAGGGTGATCTAAATCCGGACAACTCGGATGTCGA

CAAACTGTTCATCCAGTTAGTACAAACCTATAATC

AGTTGTTTGAAGAGAACCCTATAAATGCAAGTGGC

GTGGATGCGAAGGCTATTCTTAGCGCCCGCCTCTC

TAAATCCCGACGGCTAGAAAACCTGATCGCACAAT

TACCCGGAGAGAAGAAAAATGGGTTGTTCGGTAAC

CTTATAGCGCTCTCACTAGGCCTGACACCCAAATTT

TAAGTCGAACTTCGACTTAGCTGAAGATGCCAAAT

TGCAGCTTAGTAAGGACACGTACGATGACGATCTC

GACAATCTACTGGCACAAATTGGAGATCAGTATGC

GGACTTATTTTTTGGCTGCCAAAAACCTTAGCGATG

CAATCCTCCTATCTGACATACTGAGAGTTAATACT

GAGATTACCAAGGCGCCGTTATCCGCTTCAATGAT

CAAAAGGTACGATGAACATCACCAAGACTTGACAC

TTCTCAAGGCCCTAGTCCGTCAGCAACTGCCTGAG

AAATATAAGGAAATATTCTTTGATCAGTCGAAAAA

CGGGTACGCAGGTTATATTGACGGCGGAGCGAGTC

AAGAGGAATTCTACAAGTTTATCAAACCCATATTA

GAGAAGATGGATGGGACGGAAGAGTTGCTTGTAAA

ACTCAATCGCGAAGATCTACTGCGAAAGCAGCGGA

CTTTCGACAACGGTAGCATTCCACATCAAATCCAC

TTAGGCGAATTGCATGCTATACTTAGAAGGCAGGA

GGATTTTTATCCGTTCCTCAAAGACAATCGTGAAA

AGATTGAGAAAATCCTAACCTTTCGCATACCTTAC

TATGTGGGACCCCTGGCCCGAGGGAACTCTCGGTT

CGCATGGATGACAAGAAAGTCCGAAGAAACGATTA

CTCCCTGGAATTTTGAGGAAGTTGTCGATAAAGGT

GCGTCAGCTCAATCGTTCATCGAGAGGATGACCGC

CTTTGACAAGAATTTACCGAACGAAAAAGTATTGC

CTAAGCACAGTTTACTTTACGAGTATTTCACAGTG

TACAATGAACTCACGAAAGTTAAGTATGTCACTGA

GGGCATGCGTAAACCCGCCTTTCTAAGCGGAGAAC

AGAAGAAAGCAATAGTAGATCTGTTATTCAAGACC

AACCGCAAAGTGACAGTTAAGCAATTGAAAGAGGA

CTACTTTAAGAAAATTGAATGCTTCGATTCTGTCG

-continued

```
AGATCTCCGGGGTAGAAGATCGATTTAATGCGTCA

CTTGGTACGTATCATGACCTCCTAAAGATAATTAA

AGATAAGGACTTCCTGGATAACGAAGAGAATGAAG

ATATCTTAGAAGATATAGTGTTGACTCTTACCCTC

TTTGAAGATCGGGAAATGATTGAGGAAAGACTAAA

AACATACGCTCACCTGTTCGACGATAAGGTTATGA

AACAGTTAAAGAGGCGTCGCTATACGGGCTGGGGA

GCCTTGTCGCGGAAACTTATCAACGGGATAAGAGA

CAAGCAAAGTGGTAAAACTATTCTCGATTTTCTAA

AGAGCGACGGCTTCGCCAATAGGAACTTTATGGCC

CTGATCCATGATGACTCTTTAACCTTCAAAGAGGA

TATACAAAAGGCACAGGTTTCCGGACAAGGGGACT

CATTGCACGAACATATTGCGAATCTTGCTGGTTCG

CCAGCCATCAAAAAGGGCATACTCCAGACAGTCAA

AGTAGTGGATGAGCTAGTTAAGGTCATGGGACGTC

ACAAACCGGAAAACATTGTAATCGAGATGGCACGC

GAAAATCAAACGACTCAGAAGGGGCAAAAAACAG

TCGAGAGCGGATGAAGAGAATAGAAGAGGGTATTA

AAGAACTGGGCAGCCAGATCTTAAAGGAGCATCCT

GTGGAAAATACCCAATTGCAGAACGAGAAACTTTA

CCTCTATTACCTACAAAATGGAAGGGACATGTATG

TTGATCAGGAACTGGACATAAACCGTTTATCTGAT

TACGACGTCGATCACATTGTACCCCAATCCTTTTT

GAAGGACGATTCAATCGACAATAAAGTGCTTACAC

GCTCGGATAAGAACCGAGGGAAAAGTGACAATGTT

CCAAGCGAGGAAGTCGTAAAGAAAATGAAGAACTA

TTGGCGGCAGCTCCTAAATGCGAAACTGATAACGC

AAAGAAAGTTCGATAACTTAACTAAAGCTGAGAGG

GGTGGCTTGTCTGAACTTGACAAGGCCGGATTTAT

TAAACGTCAGCTCGTGGAAACCCGCGCCATCACAA

AGCATGTTGCGCAGATACTAGATTCCCGAATGAAT

ACGAAATACGACGAGAACGATAAGCTGATTCGGGA

AGTCAAAGTAATCACTTTAAAGTCAAAATTGGTGT

CGGACTTCAGAAAGGATTTTCAATTCTATAAAGTT

AGGGAGATAAATAACTACCACCATGCGCACGACGC

TTATCTTAATGCCGTCGTAGGGACCGCACTCATTA

AGAAATACCCGAAGCTAGAAAGTGAGTTTGTGTAT

GGTGATTACAAAGTTTATGACGTCCGTAAGATGAT

CGCGAAAAGCGAACAGGAGATAGGCAAGGCTACAG

CCAAATACTTCTTTTATTCTAACATTATGAATTTC

TTTAAGACGGAAATCACTCTGGCAAACGGAGAGAT
```

-continued

```
ACGCAAACGACCTTTAATTGAAACCAATGGGGAGA

CAGGTGAAATCGTATGGGATAAGGGCCGGGACTTC

GCGACGGTGAGAAAAGTTTTGTCCATGCCCCAAGT

CAACATAGTAAAGAAAACTGAGGTGCAGACCGGAG

GGTTTTCAAAGGAATCGATTCTTCCAAAAAGGAAT

AGTGATAAGCTCATCGCTCGTAAAAAGGACTGGGA

CCCGAAAAAGTACGGTGGCTTCGATAGCCCTACAG

TTGCCTATTCTGTCCTAGTAGTGGCAAAAGTTGAG

AAGGGAAAATCCAAGAAACTGAAGTCAGTCAAAGA

ATTATTGGGGATAACGATTATGGAGCGCTCGTCTT

TTGAAAAGAACCCCATCGACTTCCTTGAGGCGAAA

GGTTACAAGGAAGTAAAAAAGGATCTCATAATTAA

ACTACCAAAGTATAGTCTGTTTGAGTTAGAAAATG

GCCGAAAACGGATGTTGGCTAGCGCCGGAGAGCTT

CAAAAGGGGAACGAACTCGCACTACCGTCTAAATA

CGTGAATTTCCTGTATTTAGCGTCCCATTACGAGA

AGTTGAAAGGTTCACCTGAAGATAACGAACAGAAG

CAACTTTTTGTTGAGCAGCACAAACATTATCTCGA

CGAAATCATAGAGCAAATTTCGGAATTCAGTAAGA

GAGTCATCCTAGCTGATGCCAATCTGGACAAAGTA

TTAAGCGCATACAACAAGCACAGGGATAAACCCAT

ACGTGAGCAGGCGGAAAATATTATCCATTTGTTTA

CTCTTACCAACCTCGGCGCTCCAGCCGCATTCAAG

TATTTTGACACAACGATAGATCGCAAACGATACAC

TTCTACCAAGGAGGTGCTAGACGCGACACTGATTC

ACCAATCCATCACGGGATTATATGAAACTCGGATA

GATTTGTCACAGCTTGGGGGTGACGGATCCCCCAA

GAAGAAGAGGAAAGTCTCGAGCGACTAGAAAGACC

ATGACGGTGATTATAAAGATCATGACATCGATTAC

AAGGATGACGATGACAAGGCAAGCTTGCAGGATGA

CCGGTCATCATCACCATCACCATTGAGT
```

VSW-3 RNAP coding sequence

SEQ ID NO: 9

```
ATGAACCAGATCGAGCTAGAACAGGAAATGATTGA

CGGTGGCCGGGCGAAGATGTTCGGCTCATTCAATC

GCAACGAAGAGCAAGGAGCGGCGCACAACAACCCA

TACGCCGCAGCGGTGTACCGGCGATTCGTGCAACC

TCTGGCCGATCAAATCGACGCCTACTGCGGTGAGG

TCAAGCGCGGCGTGATGGCGGCAGGCAAAGCCCTG

CTGCGCCCGCATGACCCGATGGTGTTGGCGTTCAT

GACCGTTCGCATGGTCATGGACACCACGCTGCAAT
```

-continued

CGAAGGACAACGCACCAACCGCTGTGGCCCGAGCC

TTGGGCCAGAGCATCTACGGGGAGACTCTGCTCGC

CAAGTTTGAGCAGGTCGAACCCGACCTATACTTCA

CGCTGGTCAATGACTTTGAGCGGCGTATGACCAAG

TCGGAGCGGCACCGGCTGACGGTTTTCAAGATGCA

GGCCGAGAAGAACGGCGTACCGCTGCCTGTGTGGT

CGCCAGAGGACAAGTTGGCCATCGGCACTATCTTG

CTCTACCTTGCCCGCGATGTCGGGCTGGTGGAGAT

CACAGAGGTGCGCAAGGGCAAGAAGACTGTGCGCG

AGTACAACATGACGCCGGATGTGGCGGGCATGCTT

GACAACATCAAGGACTTTGTGGCAGGGGCCAGCCC

GATGGTGCTGCCTTGTGTGGTGCCTCCGGTGCCAT

GGACTGATGCCAACAACGGAGGATACCACACACCG

GGCATGCGCCGCATAAGCCCCTGCTGCATCCGTGG

GCGACCGCGAGTCGAAGACCTGACCGATGTACCGG

ACATCCCGTTGCGTGCGCTCAACATCCTCCAGAGC

CGCCCATGGCGCATCAATCGCATGGTGTTGGACGC

GGTGGATCTGGTGGGCCAGCGGTTCGACGTGGGTG

AGGTGCTGGCACAGGCCGAGCTGCCGAAGCCGAAG

TCGCTTCTGTGGCTGGACGATGTGCCGAAGGAAGA

AATGAACCCCGCGCAACTGGCCGAGTTCGGTGCGT

GGAAGATCGAGATGCGCGAGTGGTACACCGAGAAC

AAGAGCAGGGGCGTGCAGTGGGGCCGGTACTATGA

GGCGCTGCGAGTAGCCCGCAAGTTCAAGGACTTGC

CGTTCTGGTTCGTGTACCAATACGACTACCGAGGC

CGAGCATATGCGAACACGAGGGGCGTTAGCCCGCA

AGGTTCAGATCTCCAGAAGGCGCTGCTTATGGCAG

ACGTTGGCGTCCCAATCGCCGACGAACGAGCCAAG

TTCTGGTTCTACACAGCCGGAGCAAACCGGTTCGG

GTACGACAAAGCCACACTGGCAGAGAGGTACGAAT

GGACTGTAGAACGCTCGGAAATGATCTGTGCTATT

GCTGCCGATCCCGTAGCCAACAGGCAATGGACGGA

GGCGGACAACCCGTTCCAGTTTCTCGCATGGTGCT

TCGAGTTCGCCCAGTACACGGCAATGCCCGAGAGC

TTCTTATCTCGCCTCGCTCTTGGACAGGATGGGAG

CTGCAACGGGCTACAGCACTTCTCAGCGATGTTGC

GCGACGAAGTGGGTGGACTCGCGACCAACTTAGTG

CCCTCTACAACGCAGCAGGACATCTATCGACTGGT

AGCTGTGGAGACAACGCGGTTGTTACAAGCTATGC

CTCACGAGAACTGCGAGTTCACGCTGAAGTGGAAG

CTGCACAGCCTGTCCCGCGACTTAGTCAAACGAAG

-continued

CGTTATGACTTTGCCGTATGGATCGACGAGGTTCA

GTTGTGCTGACTTCATCTACACCGAGTACATGGCG

AAGCACAAGGCGCCGGAGTTCGCCAAGGGCGACTA

CCAGAAGGCCGCTCGCTGGCTGAGCGTACCGGTGT

GGGACGCAATCGGCAACGTAGTGGTCAAGGCAAGA

GAGGCGATGGCATGGCTTCAGAACGCCTCTGACGA

GCTGATAGACGCCGGGATCGACGAGATCTACTGGC

GGTCGCCAAGCGGATTCATGGTTCGGCAACGGTAC

GGCAAGGAAGAATTCGTTCTTGTCAAGACTCGATT

GGCTGGCGGAGTCAGAATTCGGCCAACCATCAAGC

TGGAGCTAGAGGAACCATGCAAGCGCCGGCACCGG

AACGGGATAGCTCCCAACTTCGTTCACAGCCACGA

CGCCGCGCACATGCACCTCCTGATCTGCGCCGCCG

AGGATCATGGGCTGGGCCATCTGGCATTCATCCAT

GACGACTACGGTACGACTGCGGATGGTACTGAAAC

GCTCCACAAGCTCATCAGGGCGACGTTCGTTGCCA

TGTACGAGCAAGGGTGCCCATTGACCGCATTCCGC

GACACATACGGCATCACAGAAGATCTCCCGGAACG

CGGTGATCTCGACCTGAATCTGGTTCACGATTCCA

CGTATTTCTTCGCCTGA sox7 RNA coding sequence

SEQ ID NO: 10

GGGAGACCCTCGAGGACAGATCGCCTGGAGACGGC

AAGAGCCGCCACCATGAAAAGGCCGGCGGCCACGA

AAAAGGCCGGCCAGGCAAAAAAGAAAAAGGGTTCT

GGAGCTTCGCTGCTGGGAGCCTACCCTTGGCCCGA

GGGTCTCGAGTGCCCGGCCCTGGACGCCGAGCTGT

CGGATGGACAATCGCCGCCGGCCGTCCCCCGGCCC

CCGGGGGACAAGGGCTCCGAGAGCCGTATCCGGCG

GCCCATGAACGCCTTCATGGTTTGGGCCAAGGACG

AGAGGAAACGGCTGGCAGTGCAGAACCCGGACCTG

CACAACGCCGAGCTCAGCAAGATGCTGGGAAAGTC

GTGGAAGGCGCTGACGCTGTCCCAGAAGAGGCCGT

ACGTGGACGAGGCGGAGCGGCTGCGCCTGCAGCAC

ATGCAGGACTACCCCAACTACAAGTACCGGCCGCG

CAGGAAGAAGCAGGCCAAGCGGCTGTGCAAGCGCG

TGGACCCGGGCTTCCTTCTGAGCTCCCTCTCCCGG

GACCAGAACGCCCTGCCGGAGAAGAGAAGCGGCAG

CCGGGGGGCGCTGGGGGAGAAGGAGGACAGGGGTG

AGTACTCCCCCGGCACTGCCCTGCCCAGCCTCCGG

GGCTGCTACCACGAGGGGCCGGCTGGTGGTGGCGG

-continued

CGGCGGCACCCCGAGCAGTGTGGACACGTACCCGT

ACGGGCTGCCCACACCTCCTGAAATGTCTCCCCTG

GACGTGCTGGAGCCGGAGCAGACCTTCTTCTCCTC

CCCCTGCCAGGAGGAGCATGGCCATCCCCGCCGCA

TCCCCCACCTGCCAGGGCACCCGTACTCACCGGAG

TACGCCCCAAGCCCTCTCCACTGTAGCCACCCCCT

GGGCTCCCTGGCCCTTGGCCAGTCCCCCGGCGTCT

CCATGATGTCCCCTGTACCCGGCTGTCCCCCATCT

CCTGCCTATTACTCCCCGGCCACCTACCACCCACT

CCACTCCAACCTCCAAGCCCACCTGGGCCAGCTTT

CCCCGCCTCCTGAGCACCCTGGCTTCGACGCCCTG

GATCAACTGAGCCAGGTGGAACTCCTGGGGGACAT

GGATCGCAATGAATTCGACCAGTATTTGAACACTC

CTGGCCACCCAGACTCCGCCACAGGGGCCATGGCC

CTCAGTGGGCATGTTCCGGTCTCCCAGGTGACACC

AACGGGTCCCACAGAGACCAGCCTCATCTCCGTCC

TGGCTGATGCCACGGCCACGTACTACAACAGCTAC

AGTGTGTCAGGATCCCCCAAGAAGAAGAGGAAAGT

CTCGAGCGACTAGAAAGACCATGACGGTGATTATA

AAGATCATGACATCGATTACAAGGATGACGATGAC

AAGGCAAGCTTGCAGGATGACCGGTCATCATCACC

ATCACCATTGAGT

Tpase RNA coding sequence

SEQ ID NO: 11

GGGAGAGCCGCCACCATGGAGGAAGTATGTGATTC

ATCAGCAGCTGCGAGCAGCACAGTCCAAAATCAGC

CACAGGATCAAGAGCACCCGTGGCCGTATCTTCGC

GAATTCTTTTCTTTAAGTGGTGTAAATAAAGATTC

ATTCAAGATGAAATGTGTCCTCTGTCTCCCGCTTA

ATAAAGAAATATCGGCCTTCAAAAGTTCGCCATCA

AACCTAAGGAAGCATATTGAGAGAATGCACCCAAA

TTACCTCAAAAACTACTCTAAATTGACAGCACAGA

AGAGAAAGATCGGGACCTCCACCCATGCTTCCAGC

AGTAAGCAACTGAAAGTTGACTCAGTTTTCCCAGT

CAAACATGTGTCTCCAGTCACTGTGAACAAAGCTA

TATTAAGGTACATCATTCAAGGACTTCATCCTTTC

AGCACTGTTGATCTGCCATCATTTAAAGAGCTGAT

TAGTACACTGCAGCCTGGCATTTCTGTCATTACAA

GGCCTACTTTACGCTCCAAGATAGCTGAAGCTGCT

CTGATCATGAAACAGAAAGTGACTGCTGCCATGAG

TGAAGTTGAATGGATTGCAACCACAACGGATTGTT

GGACTGCACGTAGAAAGTCATTCATTGGTGTAACT

-continued

GCTCACTGGATCAACCCTGGAAGTCTTGAAAGACA

TTCCGCTGCACTTGCCTGCAAAAGATTAATGGGCT

CTCATACTTTTGAGGTACTGGCCAGTGCCATGAAT

GATATCCACTCAGAGTATGAAATACGTGACAAGGT

TGTTTGCACAACCACAGACAGTGGTTCCAACTTTA

TGAAGGCTTTCAGAGTTTTTGGTGTGGAAAACAAT

GATATCGAGACTGAGGCAAGAAGGTGTGAAAGTGA

TGACACTGATTCTGAAGGCTGTGGTGAGGGAAGTG

ATGGTGTGGAATTCCAAGATGCCTCACGAGTCCTG

GACCAAGACGATGGCTTCGAATTCCAGCTACCAAA

ACATCAAAAGTGTGCCTGTCACTTACTTAACCTAG

TCTCAAGCGTTGATGCCCAAAAAGCTCTCTCAAAT

GAACACTACAAGAAACTCTACAGATCTGTCTTTGG

CAAATGCCAAGCTTTATGGAATAAAAGCAGCCGAT

CGGCTCTAGCAGCTGAAGCTGTTGAATCAGAAAGC

CGGCTTCAGCTTTTAAGGCCAAACCAAACGCGGTG

GAATTCAACTTTTATGGCTGTTGACAGAATTCTTC

AAATTTGCAAAGAAGCAGGAGAAGGCGCACTTCGG

AATATATGCACCTCTCTTGAGGTTCCAATGTTTAA

TCCAGCAGAAATGCTGTTCTTGACAGAGTGGGCCA

ACACAATGCGTCCAGTTGCAAAAGTACTCGACATC

TTGCAAGCGGAAACGAATACACAGCTGGGGTGGCT

GCTGCCTAGTGTCCATCAGTTAAGCTTGAAACTTC

AGCGACTCCACCATTCTCTCAGGTACTGTGACCCA

CTTGTGGATGCCCTACAACAAGGAATCCAAACACG

ATTCAAGCATATGTTTGAAGATCCTGAGATCATAG

CAGCTGCCATCCTTCTCCCTAAATTTCGGACCTCT

TGGACAAATGATGAAACCATCATAAAACGAGGCAT

GGACTACATCAGAGTGCATCTGGAGCCTTTGGACC

ACAAGAAGGAATTGGCCAACAGTTCATCTGATGAT

GAAGATTTTTTCGCTTCTTTGAAACCGACAACACA

TGAAGCCAGCAAAGAGTTGGATGGATATCTGGCCT

GTGTTTCAGACACCAGGGAGTCTCTGCTCACGTTT

CCTGCTATTTGCAGCCTCTCTATCAAGACTAATAC

ACCTCTTCCCGCATCGGCTGCCTGTGAGAGGCTTT

TCAGCACTGCAGGATTGCTTTTCAGCCCCAAAAGA

GCTAGGCTTGACACTAACAATTTTGAGAATCAGCT

TCTACTGAAGTTAAATCTGAGGTTTTACAACTTTG

AGGGATCCCCCAAGAAGAAGAGGAAAGTCTCGAGC

GACTAGAAAGACCATGACGGTGATTATAAAGATCA

-continued

TGACATCGATTACAAGGATGACGATGACAAGGCAA

GCTTGCAGGATGACCGGTCATCATCACCATCACCA

TTGAGT copGFP RNA coding sequence

SEQ ID NO: 12

GGGAGAGCCGCCACCATGGAGAGCGACGAGAGCGG

CCTGCCCGCCATGGAGATCGAGTGCCGCATCACCG

GCACCCTGAACGGCGTGGAGTTCGAGCTGGTGGGC

GGCGGAGAGGGCACCCCCAAGCAGGGCCGCATGAC

CAACAAGATGAAGAGCACCAAAGGCGCCCTGACCT

TCAGCCCCTACCTGCTGAGCCACGTGATGGGCTAC

GGCTTCTACCACTTCGGCACCTACCCCAGCGGCTA

CGAGAACCCCTTCCTGCACGCCATCAACAACGGCG

GCTACACCAACACCCGCATCGAGAAGTACGAGGAC

GGCGGCGTGCTGCACGTGAGCTTCAGCTACCGCTA

CGAGGCCGGCCGCGTGATCGGCGACTTCAAGGTGG

TGGGCACCGGCTTCCCCGAGGACAGCGTGATCTTC

-continued

ACCGACAAGATCATCCGCAGCAACGCCACCGTGGA

GCACCTGCACCCCATGGGCGATAACGTGCTGGTGG

GCAGCTTCGCCCGCACCTTCAGCCTGCGCGACGGC

GGCTACTACAGCTTCGTGGTGGACAGCCACATGCA

CTTCAAGAGCGCCATCCACCCCAGCATCCTGCAGA

ACGGGGGCCCCATGTTCGCCTTCCGCCGCGTGGAG

GAGCTGCACAGCAACACCGAGCTGGGCATCGTGGA

GTACCAGCACGCCTTCAAGACCCCCATCGCCTTCG

CCAGATCCCGCGCTCAGTCGTCCAATTCTGCCGTG

GACGGCACCGCCGGACCCGGCTCCACCGGATCTCG

CGGATCCCCCAAGAAGAAGAGGAAAGTCTCGAGCG

ACTAGAAAGACCATGACGGTGATTATAAAGATCAT

GACATCGATTACAAGGATGACGATGACAAGGCAAG

CTTGCAGGATGACCGGTCATCATCACCATCACCAT

TGAGT

---

What is claimed is:

1. A method for performing an in vitro transcription reaction, comprising incubating a RNA polymerase with a DNA molecule and nucleotides for a sufficient time to produce transcripts, wherein the RNA polymerase comprises a polypeptide comprising
   1) an amino acid sequence of SEQ ID NO:5, or
   2) an amino acid sequence having at least 80% sequence identity to SEQ ID NO:5 and possessing an RNA polymerase activity,
   and wherein the DNA molecule comprises a promoter sequence for the RNA polymerase and a DNA sequence to be transcribed.

2. The method of claim 1, wherein the RNA polymerase is isolated from a psychrophilic bacteriophage, or is encoded by a gene of a psychrophilic bacteriophage.

3. The method of claim 2, wherein the psychrophilic bacteriophage is bacteriophage VSW-3.

4. The method of claim 1, wherein the RNA polymerase comprises an amino acid sequence of SEQ ID NO:6.

5. The method of claim 1, wherein the incubating is performed at 4-37° C.

6. The method of claim 1, wherein the promoter sequence for the RNA polymerase has a nucleotide sequence of SEQ ID NO: 1, 2, 3 or 4.

7. The method of claim 1, wherein the incubating is performed in a buffer containing 5 mM DTT.

8. The method of claim 1, wherein a class II transcription terminator sequence ATCTGTT does not mediate a transcriptional termination of the transcription reaction.

9. The method of claim 1, wherein the DNA sequence to be transcribed comprises a coding sequence for Cas9.

10. The method of claim 9, wherein the coding sequence comprises a nucleotide sequence of SEQ ID NO: 9.

11. The method of claim 1, wherein the nucleotides comprise pseudoUTP, 5mCTP and/or 5moUTP.

12. The method of claim 1, wherein the nucleotides comprise m5CTP, m6ATP, 2'-F-dATP and/or 2'-F-dUTP.

13. The method of claim 1, wherein the RNA polymerase comprises an amino acid sequence of SEQ ID NO: 6, and the nucleotides comprises 2'-F-dATP and/or 2'-F-dUTP.

* * * * *

SEQUENCE LISTING

<160> NUMBER OF SEQ ID NOS: 45

<210> SEQ ID NO 1
<211> LENGTH: 18
<212> TYPE: DNA
<213> ORGANISM: Artificial Sequence
<220> FEATURE:
<223> OTHER INFORMATION: Promoter for VSW-3 RNAP

<400> SEQUENCE: 1
ttaattgggc cacctata                                                     18

<210> SEQ ID NO 2
<211> LENGTH: 17
<212> TYPE: DNA
<213> ORGANISM: Artificial Sequence
<220> FEATURE:
<223> OTHER INFORMATION: Promoter for VSW-3 RNAP

<400> SEQUENCE: 2
taattgggcc acctata                                                      17

<210> SEQ ID NO 3
<211> LENGTH: 16
<212> TYPE: DNA
<213> ORGANISM: Artificial Sequence
<220> FEATURE:
<223> OTHER INFORMATION: Promoter for VSW-3 RNAP

<400> SEQUENCE: 3
aattgggcca cctata                                                       16

<210> SEQ ID NO 4
<211> LENGTH: 15
<212> TYPE: DNA
<213> ORGANISM: Artificial Sequence
<220> FEATURE:

<223> OTHER INFORMATION: Promoter

<400> SEQUENCE: 4
attgggccac ctata                                                        15

<210> SEQ ID NO 5
<211> LENGTH: 798
<212> TYPE: PRT
<213> ORGANISM: Artificial Sequence
<220> FEATURE:
<223> OTHER INFORMATION: VSW-3 RNAP protein sequence-WT

<400> SEQUENCE: 5

Met Asn Gln Ile Glu Leu Glu Gln Glu Met Ile Asp Gly Gly Arg Ala
1               5                   10                  15

Lys Met Phe Gly Ser Phe Asn Arg Asn Glu Glu Gln Gly Ala Ala His
            20                  25                  30

Asn Asn Pro Tyr Ala Ala Ala Val Tyr Arg Arg Phe Val Gln Pro Leu
        35                  40                  45

Ala Asp Gln Ile Asp Ala Tyr Cys Gly Glu Val Lys Arg Gly Val Met
    50                  55                  60

Ala Ala Gly Lys Ala Leu Leu Arg Pro His Asp Pro Met Val Leu Ala
65                  70                  75                  80

Phe Met Thr Val Arg Met Val Met Asp Thr Thr Leu Gln Ser Lys Asp
                85                  90                  95

Asn Ala Pro Thr Ala Val Ala Arg Ala Leu Gly Gln Ser Ile Tyr Gly
            100                 105                 110

Glu Thr Leu Leu Ala Lys Phe Glu Gln Val Glu Pro Asp Leu Tyr Phe
            115                 120                 125

Thr Leu Val Asn Asp Phe Glu Arg Arg Met Thr Lys Ser Glu Arg His
        130                 135                 140

Arg Leu Thr Val Phe Lys Met Gln Ala Glu Lys Asn Gly Val Pro Leu
145                 150                 155                 160

Pro Val Trp Ser Pro Glu Asp Lys Leu Ala Ile Gly Thr Ile Leu Leu
                165                 170                 175

Tyr Leu Ala Arg Asp Val Gly Leu Val Glu Ile Thr Glu Val Arg Lys
            180                 185                 190

Gly Lys Lys Thr Val Arg Glu Tyr Asn Met Thr Pro Asp Val Ala Gly
            195                 200                 205

Met Leu Asp Asn Ile Lys Asp Phe Val Ala Gly Ala Ser Pro Met Val
        210                 215                 220

Leu Pro Cys Val Val Pro Pro Val Pro Trp Thr Asp Ala Asn Asn Gly
225                 230                 235                 240

Gly Tyr His Thr Pro Gly Met Arg Arg Ile Ser Pro Cys Cys Ile Arg
                245                 250                 255

Gly Arg Pro Arg Val Glu Asp Leu Thr Asp Val Pro Asp Ile Pro Leu
            260                 265                 270

Arg Ala Leu Asn Ile Leu Gln Ser Arg Pro Trp Arg Ile Asn Arg Met
            275                 280                 285

Val Leu Asp Ala Val Asp Leu Val Gly Gln Arg Phe Asp Val Gly Glu
        290                 295                 300

Val Leu Ala Gln Ala Glu Leu Pro Lys Pro Lys Ser Leu Leu Trp Leu
305                 310                 315                 320

Asp Asp Val Pro Lys Glu Glu Met Asn Pro Ala Gln Leu Ala Glu Phe
                325                 330                 335

-continued

```
Gly Ala Trp Lys Ile Glu Met Arg Glu Trp Tyr Thr Glu Asn Lys Ser
            340                 345                 350

Arg Gly Val Gln Trp Gly Arg Tyr Tyr Glu Ala Leu Arg Val Ala Arg
            355                 360                 365

Lys Phe Lys Asp Leu Pro Phe Trp Phe Val Tyr Gln Tyr Asp Tyr Arg
            370                 375                 380

Gly Arg Ala Tyr Ala Asn Thr Arg Gly Val Ser Pro Gln Gly Ser Asp
385                 390                 395                 400

Leu Gln Lys Ala Leu Leu Met Ala Asp Val Gly Val Pro Ile Ala Asp
                405                 410                 415

Glu Arg Ala Lys Phe Trp Phe Tyr Thr Ala Gly Ala Asn Arg Phe Gly
                420                 425                 430

Tyr Asp Lys Ala Thr Leu Ala Glu Arg Tyr Glu Trp Thr Val Glu Arg
            435                 440                 445

Ser Glu Met Ile Cys Ala Ile Ala Ala Asp Pro Val Ala Asn Arg Gln
            450                 455                 460

Trp Thr Glu Ala Asp Asn Pro Phe Gln Phe Leu Ala Trp Cys Phe Glu
465                 470                 475                 480

Phe Ala Gln Tyr Thr Ala Met Pro Glu Ser Phe Leu Ser Arg Leu Ala
                485                 490                 495

Leu Gly Gln Asp Gly Ser Cys Asn Gly Leu Gln His Phe Ser Ala Met
            500                 505                 510

Leu Arg Asp Glu Val Gly Gly Leu Ala Thr Asn Leu Val Pro Ser Thr
            515                 520                 525

Thr Gln Gln Asp Ile Tyr Arg Leu Val Ala Val Glu Thr Thr Arg Leu
            530                 535                 540

Leu Gln Ala Met Pro His Glu Asn Cys Glu Phe Thr Leu Lys Trp Lys
545                 550                 555                 560

Leu His Ser Leu Ser Arg Asp Leu Val Lys Arg Ser Val Met Thr Leu
                565                 570                 575

Pro Tyr Gly Ser Thr Arg Phe Ser Cys Ala Asp Phe Ile Tyr Thr Glu
            580                 585                 590

Tyr Met Ala Lys His Lys Ala Pro Glu Phe Ala Lys Gly Asp Tyr Gln
            595                 600                 605

Lys Ala Ala Arg Trp Leu Ser Val Pro Val Trp Asp Ala Ile Gly Asn
            610                 615                 620

Val Val Val Lys Ala Arg Glu Ala Met Ala Trp Leu Gln Asn Ala Ser
625                 630                 635                 640

Asp Glu Leu Ile Asp Ala Gly Ile Asp Glu Ile Tyr Trp Arg Ser Pro
                645                 650                 655

Ser Gly Phe Met Val Arg Gln Arg Tyr Gly Lys Glu Glu Phe Val Leu
            660                 665                 670

Val Lys Thr Arg Leu Ala Gly Gly Val Arg Ile Arg Pro Thr Ile Lys
            675                 680                 685

Leu Glu Leu Glu Glu Pro Cys Lys Arg Arg His Arg Asn Gly Ile Ala
            690                 695                 700

Pro Asn Phe Val His Ser His Asp Ala Ala His Met His Leu Leu Ile
705                 710                 715                 720

Cys Ala Ala Glu Asp His Gly Leu Gly His Leu Ala Phe Ile His Asp
                725                 730                 735

Asp Tyr Gly Thr Thr Ala Asp Gly Thr Glu Thr Leu His Lys Leu Ile
            740                 745                 750

Arg Ala Thr Phe Val Ala Met Tyr Glu Gln Gly Cys Pro Leu Thr Ala
```

-continued

```
          755                  760                  765
Phe Arg Asp Thr Tyr Gly Ile Thr Glu Asp Leu Pro Glu Arg Gly Asp
    770                  775                  780

Leu Asp Leu Asn Leu Val His Asp Ser Thr Tyr Phe Phe Ala
785                  790                  795

<210> SEQ ID NO 6
<211> LENGTH: 798
<212> TYPE: PRT
<213> ORGANISM: Artificial Sequence
<220> FEATURE:
<223> OTHER INFORMATION: VSW-3 RNAP protein sequence-Y578F

<400> SEQUENCE: 6

Met Asn Gln Ile Glu Leu Glu Gln Glu Met Ile Asp Gly Gly Arg Ala
1               5                  10                  15

Lys Met Phe Gly Ser Phe Asn Arg Asn Glu Glu Gln Gly Ala Ala His
            20                  25                  30

Asn Asn Pro Tyr Ala Ala Ala Val Tyr Arg Arg Phe Val Gln Pro Leu
        35                  40                  45

Ala Asp Gln Ile Asp Ala Tyr Cys Gly Glu Val Lys Arg Gly Val Met
    50                  55                  60

Ala Ala Gly Lys Ala Leu Leu Arg Pro His Asp Pro Met Val Leu Ala
65                  70                  75                  80

Phe Met Thr Val Arg Met Val Met Asp Thr Thr Leu Gln Ser Lys Asp
            85                  90                  95

Asn Ala Pro Thr Ala Val Ala Arg Ala Leu Gly Gln Ser Ile Tyr Gly
            100                 105                 110

Glu Thr Leu Leu Ala Lys Phe Glu Gln Val Glu Pro Asp Leu Tyr Phe
        115                 120                 125

Thr Leu Val Asn Asp Phe Glu Arg Arg Met Thr Lys Ser Glu Arg His
    130                 135                 140

Arg Leu Thr Val Phe Lys Met Gln Ala Glu Lys Asn Gly Val Pro Leu
145                 150                 155                 160

Pro Val Trp Ser Pro Glu Asp Lys Leu Ala Ile Gly Thr Ile Leu Leu
                165                 170                 175

Tyr Leu Ala Arg Asp Val Gly Leu Val Glu Ile Thr Glu Val Arg Lys
            180                 185                 190

Gly Lys Lys Thr Val Arg Glu Tyr Asn Met Thr Pro Asp Val Ala Gly
            195                 200                 205

Met Leu Asp Asn Ile Lys Asp Phe Val Ala Gly Ala Ser Pro Met Val
    210                 215                 220

Leu Pro Cys Val Val Pro Pro Val Pro Trp Thr Asp Ala Asn Asn Gly
225                 230                 235                 240

Gly Tyr His Thr Pro Gly Met Arg Arg Ile Ser Pro Cys Cys Ile Arg
                245                 250                 255

Gly Arg Pro Arg Val Glu Asp Leu Thr Asp Val Pro Asp Ile Pro Leu
            260                 265                 270

Arg Ala Leu Asn Ile Leu Gln Ser Arg Pro Trp Arg Ile Asn Arg Met
        275                 280                 285

Val Leu Asp Ala Val Asp Leu Val Gly Gln Arg Phe Asp Val Gly Glu
    290                 295                 300

Val Leu Ala Gln Ala Glu Leu Pro Lys Pro Lys Ser Leu Leu Trp Leu
305                 310                 315                 320

Asp Asp Val Pro Lys Glu Glu Met Asn Pro Ala Gln Leu Ala Glu Phe
```

-continued

```
                 325              330              335
Gly Ala Trp Lys Ile Glu Met Arg Glu Trp Tyr Thr Glu Asn Lys Ser
            340              345              350

Arg Gly Val Gln Trp Gly Arg Tyr Tyr Glu Ala Leu Arg Val Ala Arg
            355              360              365

Lys Phe Lys Asp Leu Pro Phe Trp Phe Val Tyr Gln Tyr Asp Tyr Arg
        370              375              380

Gly Arg Ala Tyr Ala Asn Thr Arg Gly Val Ser Pro Gln Gly Ser Asp
385              390              395              400

Leu Gln Lys Ala Leu Leu Met Ala Asp Val Gly Val Pro Ile Ala Asp
            405              410              415

Glu Arg Ala Lys Phe Trp Phe Tyr Thr Ala Gly Ala Asn Arg Phe Gly
            420              425              430

Tyr Asp Lys Ala Thr Leu Ala Glu Arg Tyr Glu Trp Thr Val Glu Arg
        435              440              445

Ser Glu Met Ile Cys Ala Ile Ala Ala Asp Pro Val Ala Asn Arg Gln
        450              455              460

Trp Thr Glu Ala Asp Asn Pro Phe Gln Phe Leu Ala Trp Cys Phe Glu
465              470              475              480

Phe Ala Gln Tyr Thr Ala Met Pro Glu Ser Phe Leu Ser Arg Leu Ala
            485              490              495

Leu Gly Gln Asp Gly Ser Cys Asn Gly Leu Gln His Phe Ser Ala Met
            500              505              510

Leu Arg Asp Glu Val Gly Gly Leu Ala Thr Asn Leu Val Pro Ser Thr
            515              520              525

Thr Gln Gln Asp Ile Tyr Arg Leu Val Ala Val Glu Thr Thr Arg Leu
        530              535              540

Leu Gln Ala Met Pro His Glu Asn Cys Glu Phe Thr Leu Lys Trp Lys
545              550              555              560

Leu His Ser Leu Ser Arg Asp Leu Val Lys Arg Ser Val Met Thr Leu
            565              570              575

Pro Phe Gly Ser Thr Arg Phe Ser Cys Ala Asp Phe Ile Tyr Thr Glu
            580              585              590

Tyr Met Ala Lys His Lys Ala Pro Glu Phe Ala Lys Gly Asp Tyr Gln
        595              600              605

Lys Ala Ala Arg Trp Leu Ser Val Pro Val Trp Asp Ala Ile Gly Asn
        610              615              620

Val Val Val Lys Ala Arg Glu Ala Met Ala Trp Leu Gln Asn Ala Ser
625              630              635              640

Asp Glu Leu Ile Asp Ala Gly Ile Asp Glu Ile Tyr Trp Arg Ser Pro
            645              650              655

Ser Gly Phe Met Val Arg Gln Arg Tyr Gly Lys Glu Glu Phe Val Leu
            660              665              670

Val Lys Thr Arg Leu Ala Gly Gly Val Arg Ile Arg Pro Thr Ile Lys
            675              680              685

Leu Glu Leu Glu Glu Pro Cys Lys Arg Arg His Arg Asn Gly Ile Ala
        690              695              700

Pro Asn Phe Val His Ser His Asp Ala Ala His Met His Leu Leu Ile
705              710              715              720

Cys Ala Ala Glu Asp His Gly Leu Gly His Leu Ala Phe Ile His Asp
            725              730              735

Asp Tyr Gly Thr Thr Ala Asp Gly Thr Glu Thr Leu His Lys Leu Ile
            740              745              750
```

-continued

```
Arg Ala Thr Phe Val Ala Met Tyr Glu Gln Gly Cys Pro Leu Thr Ala
      755                 760                 765

Phe Arg Asp Thr Tyr Gly Ile Thr Glu Asp Leu Pro Glu Arg Gly Asp
      770                 775                 780

Leu Asp Leu Asn Leu Val His Asp Ser Thr Tyr Phe Phe Ala
785                 790                 795

<210> SEQ ID NO 7
<211> LENGTH: 103
<212> TYPE: DNA
<213> ORGANISM: Artificial Sequence
<220> FEATURE:
<223> OTHER INFORMATION: sgRNA coding sequence

<400> SEQUENCE: 7
gggcacgggc agcttgccgg gttttagagc tagaaatagc aagttaaaat aaggctagtc      60
cgttatcaac ttgaaaaagt ggcaccgagt cggtgctttt ttt                      103

<210> SEQ ID NO 8
<211> LENGTH: 4263
<212> TYPE: DNA
<213> ORGANISM: Artificial Sequence
<220> FEATURE:
<223> OTHER INFORMATION: cas9 RNA coding sequence

<400> SEQUENCE: 8
gggagagccg ccaccatgga taaaaagtat tctattggtt tagacatcgg cactaattcc      60
gttggatggg ctgtcataac cgatgaatac aaagtacctt caaagaaatt taaggtgttg     120
gggaacacag accgtcattc gattaaaaag aatcttatcg gtgccctcct attcgatagt     180
ggcgaaacgg cagaggcgac tcgcctgaaa cgaaccgctc ggagaaggta tacacgtcgc     240
aagaaccgaa tatgttactt acaagaaatt tttagcaatg agatggccaa agttgacgat     300
tctttctttc accgtttgga agagtccttc cttgtcgaag aggacaagaa acatgaacgg     360 cacccatct ttggaaacat agtagatgag gtggcatatc atgaaaagta cccaacgatt     420
tatcacctca gaaaaaagct agttgactca actgataaag cggacctgag gttaatctac     480
ttggctcttg cccatatgat aaagttccgt gggcacttc tcattgaggg tgatctaaat     540
ccggacaact cggatgtcga caactgttc atccagttag tacaaaccta taatcagttg     600
tttgaagaga accctataaa tgcaagtggc gtggatgcga aggctattct tagcgcccgc     660
ctctctaaat cccgacggct agaaaacctg atcgcacaat acccggagaa gaagaaaaat     720
gggttgttcg gtaaccttat agcgctctca ctaggcctga caccaaattt taagtcgaac     780
ttcgacttag ctgaagatgc caaattgcag cttagtaagg acacgtacga tgacgatctc     840
gacaatctac tggcacaaat ggagatcag tatgcggact tattttttggc tgccaaaaac     900 cttagcgatg caatcctcct atctgacata ctgagagtta atactgagat taccaaggcg     960
ccgttatccg cttcaatgat caaaaggtac gatgaacatc accaagactt gacacttctc    1020
aaggccctag tccgtcagca actgcctgag aaatataagg aaatattctt tgatcagtcg    1080
aaaaacgggt acgcaggtta tattgacggc ggagcgagtc aagaggaatt ctacaagttt    1140
atcaaaccca tattagagaa gatggatggg acggaagagt tgcttgtaaa actcaatcgc    1200
gaagatctac tgcgaaagca gcggactttc gacaacggta gcattccaca tcaaatccac    1260
ttaggcgaat tgcatgctat acttagaagg caggaggatt tttatccgtt cctcaaagac    1320
aatcgtgaaa agattgagaa aatcctaacc tttcgcatac cttactatgt gggaccctg    1380
```

```
gcccgaggga actctcggtt cgcatggatg acaagaaagt ccgaagaaac gattactccc      1440
tggaattttg aggaagttgt cgataaaggt gcgtcagctc aatcgttcat cgagaggatg      1500
accgcctttg acaagaattt accgaacgaa aaagtattgc ctaagcacag tttactttac      1560
gagtatttca cagtgtacaa tgaactcacg aaagttaagt atgtcactga gggcatgcgt      1620
aaacccgcct ttctaagcgg agaacagaag aaagcaatag tagatctgtt attcaagacc      1680
aaccgcaaag tgacagttaa gcaattgaaa gaggactact ttaagaaaat tgaatgcttc      1740
gattctgtcg agatctccgg ggtagaagat cgatttaatg cgtcacttgg tacgtatcat      1800
gacctcctaa agataattaa agataaggac ttcctggata cgaagagaa tgaagatatc      1860 ttagaagata tagtgttgac tcttaccctc tttgaagatc gggaaatgat tgaggaaaga      1920
ctaaaaacat acgctcacct gttcgacgat aaggttatga aacagttaaa gaggcgtcgc      1980
tatacgggct ggggagcctt gtcgcggaaa cttatcaacg ggataagaga caagcaaagt      2040
ggtaaaacta ttctcgattt tctaaagagc gacggcttcg ccaataggaa ctttatggcc      2100
ctgatccatg atgactcttt aaccttcaaa gaggatatac aaaaggcaca ggtttccgga      2160
caaggggact cattgcacga acatattgcg aatcttgctg gttcgccagc catcaaaaag      2220
ggcatactcc agacagtcaa agtagtggat gagctagtta aggtcatggg acgtcacaaa      2280
ccggaaaaca ttgtaatcga gatggcacgc gaaaatcaaa cgactcagaa ggggcaaaaa      2340
aacagtcgag agcggatgaa gagaatagaa gagggtatta aagaactggg cagccagatc      2400
ttaaaggagc atcctgtgga aaatacccaa ttgcagaacg agaaacttta cctctattac      2460
ctacaaaatg gaagggacat gtatgttgat caggaactgg acataaaccg tttatctgat      2520
tacgacgtcg atcacattgt accccaatcc tttttgaagg acgattcaat cgacaataaa      2580
gtgcttacac gctcggataa gaaccgaggg aaaagtgaca atgttccaag cgaggaagtc      2640
gtaaagaaaa tgaagaacta ttggcggcag ctcctaaatg cgaaactgat aacgcaaaga      2700
aagttcgata acttaactaa agctgagagg ggtggcttgt ctgaacttga caaggccgga      2760
tttattaaac gtcagctcgt ggaaacccgc gccatcacaa agcatgttgc gcagatacta      2820
gattcccgaa tgaatacgaa atacgacgag aacgataagc tgattcggga agtcaaagta      2880
atcactttaa agtcaaaatt ggtgtcggac ttcagaaagg attttcaatt ctataaagtt      2940
agggagataa ataactacca ccatgcgcac gacgcttatc ttaatgccgt cgtagggacc      3000
gcactcatta agaaataccc gaagctagaa agtgagtttg tgtatggtga ttacaaagtt      3060
tatgacgtcc gtaagatgat cgcgaaaagc gaacaggaga taggcaaggc tacagccaaa      3120
tacttctttt attctaacat tatgaatttc tttaagacgg aaatcactct ggcaaacgga      3180
gagatacgca acgacctttt aattgaaacc aatgggaga caggtgaaat cgtatgggat      3240
aagggccggg acttcgcgac ggtgagaaaa gttttgtcca tgccccaagt caacatagta      3300
aagaaaactg aggtgcagac cggagggttt tcaaaggaat cgattcttcc aaaaaggaat      3360
agtgataagc tcatcgctcg taaaaaggac tgggacccga aaaagtacgg tggcttcgat      3420
agccctacag ttgcctattc tgtcctagta gtggcaaaag ttgagaaggg aaaatccaag      3480
aaactgaagt cagtcaaaga attattgggg ataacgatta tggagcgctc gtcttttgaa      3540
aagaacccca tcgacttcct tgaggcgaaa ggttacaagg aagtaaaaaa ggatctcata      3600
attaaactac caaagtatag tctgtttgag ttagaaaatg ccgaaaacg gatgttggct      3660 agcgccggag agcttcaaaa ggggaacgaa ctcgcactac cgtctaaata cgtgaatttc      3720
```

```
ctgtatttag cgtcccatta cgagaagttg aaaggttcac ctgaagataa cgaacagaag    3780
caactttttg ttgagcagca caaacattat ctcgacgaaa tcatagagca aatttcggaa    3840
ttcagtaaga gagtcatcct agctgatgcc aatctggaca aagtattaag cgcatacaac    3900
aagcacaggg ataaacccat acgtgagcag gcggaaaata ttatccattt gtttactctt    3960
accaacctcg gcgctccagc cgcattcaag tattttgaca caacgataga tcgcaaacga    4020
tacacttcta ccaaggaggt gctagacgcg acactgattc accaatccat cacgggatta    4080
tatgaaactc ggatagattt gtcacagctt gggggtgacg gatcccccaa gaagaagagg    4140
aaagtctcga gcgactagaa agaccatgac ggtgattata aagatcatga catcgattac    4200
aaggatgacg atgacaaggc aagcttgcag gatgaccggt catcatcacc atcaccattg    4260
agt    4263
```

<210> SEQ ID NO 9
<211> LENGTH: 2397
<212> TYPE: DNA
<213> ORGANISM: Artificial Sequence
<220> FEATURE:
<223> OTHER INFORMATION: VSW-3 RNAP coding sequence

<400> SEQUENCE: 9

```
atgaaccaga tcgagctaga acaggaaatg attgacggtg gccgggcgaa gatgttcggc     60
tcattcaatc gcaacgaaga gcaaggagcg gcgcacaaca acccatacgc cgcagcggtg    120
taccggcgat tcgtgcaacc tctggccgat caaatcgacg cctactgcgg tgaggtcaag    180
cgcggcgtga tggcggcagg caaagccctg ctgcgcccgc atgacccgat ggtgttggcg    240
ttcatgaccg ttcgcatggt catggacacc acgctgcaat cgaaggacaa cgcaccaacc    300
gctgtggccc gagccttggg ccagagcatc tacgggggaga ctctgctcgc caagtttgag    360
caggtcgaac ccgacctata cttcacgctg gtcaatgact ttgagcggcg tatgaccaag    420
tcggagcggc accggctgac ggttttcaag atgcaggccg agaagaacgg cgtaccgctg    480
cctgtgtggt cgccagagga caagttggcc atcggcacta tcttgctcta ccttgcccgc    540
gatgtcgggc tggtggagat cacagaggtg cgcaagggca agaagactgt gcgcgagtac    600
aacatgacgc cggatgtggc gggcatgctt gacaacatca aggactttgt ggcagggggcc    660 agcccgatgg tgctgccttg tgtggtgcct ccggtgccat ggactgatgc caacaacgga    720
ggataccaca caccgggcat cgccgcata agccctgct gcatccgtgg cgcaccgcga    780
gtcgaagacc tgaccgatgt accggacatc ccgttgcgtg cgctcaacat cctccagagc    840
cgcccatggc gcatcaatcg catggtgttg gacgcggtgg atctggtggg ccagcggttc    900
gacgtgggtg aggtgctggc acaggccgag ctgccgaagc cgaagtcgct tctgtggctg    960
gacgatgtgc cgaaggaaga aatgaacccc gcgcaactgg ccgagttcgg tgcgtggaag    1020
atcgagatgc gcgagtggta caccgagaac aagagcaggg gcgtgcagtg gggccggtac    1080
tatgaggcgc tgcgagtagc ccgcaagttc aaggacttgc cgttctggtt cgtgtaccaa    1140
tacgactacc gaggccgagc atatgcgaac acgaggggcg ttagcccgca aggttcagat    1200
ctccagaagg cgctgcttat ggcagacgtt ggcgtcccaa tcgccgacga acgagccaag    1260
ttctggttct acacagccgg agcaaaccgg ttcgggtacg acaaagccac actggcagag    1320
aggtacgaat ggactgtaga acgctcggaa atgatctgtg ctattgctgc cgatcccgta    1380
gccaacaggc aatggacgga ggcggacaac ccgttccagt ttctcgcatg gtgcttcgag    1440
ttcgcccagt acacggcaat gcccgagagc ttcttatctc gcctcgctct tggacaggat    1500
```

-continued

```
gggagctgca acgggctaca gcacttctca gcgatgttgc gcgacgaagt gggtggactc      1560
gcgaccaact tagtgccctc tacaacgcag caggacatct atcgactggt agctgtggag      1620
acaacgcggt tgttacaagc tatgcctcac gagaactgcg agttcacgct gaagtggaag      1680
ctgcacagcc tgtcccgcga cttagtcaaa cgaagcgtta tgactttgcc gtatggatcg      1740
acgaggttca gttgtgctga cttcatctac accgagtaca tggcgaagca caaggcgccg      1800
gagttcgcca agggcgacta ccagaaggcc gctcgctggc tgagcgtacc ggtgtgggac      1860
gcaatcggca acgtagtggt caaggcaaga gaggcgatgg catggcttca gaacgcctct      1920
gacgagctga tagacgccgg gatcgacgag atctactggc ggtcgccaag cggattcatg      1980
gttcggcaac ggtacggcaa ggaagaattc gttcttgtca agactcgatt ggctggcgga      2040
gtcagaattc ggccaaccat caagctggag ctagaggaac catgcaagcg ccggcaccgg      2100
aacgggatag ctcccaactt cgttcacagc cacgacgccg cgcacatgca cctcctgatc      2160
tgcgccgccg aggatcatgg gctgggccat ctggcattca tccatgacga ctacggtacg      2220
actgcggatg gtactgaaac gctccacaag ctcatcaggg cgacgttcgt tgccatgtac      2280
gagcaagggt gcccattgac cgcattccgc gacacatacg gcatcacaga agatctcccg      2340
gaacgcggtg atctcgacct gaatctggtt cacgattcca cgtatttctt cgcctga        2397
```

```
<210> SEQ ID NO 10
<211> LENGTH: 1413
<212> TYPE: DNA
<213> ORGANISM: Artificial Sequence
<220> FEATURE:
<223> OTHER INFORMATION: sox7 RNA coding sequence

<400> SEQUENCE: 10
```

```
gggagaccct cgaggacaga tcgcctggag acggcaagag ccgccaccat gaaaaggccg        60
gcggccacga aaaggccggg ccaggcaaaa aagaaaaagg gttctggagc ttcgctgctg       120
ggagcctacc cttggcccga gggtctcgag tgcccggccc tggacgccga gctgtcggat       180
ggacaatcgc cgccggccgt cccccggccc ccggggggaca agggctccga gagccgtatc      240
cggcggccca tgaacgcctt catggtttgg gccaaggacg agaggaaacg gctggcagtg      300
cagaacccgg acctgcacaa cgccgagctc agcaagatgc tgggaaagtc gtggaaggcg      360
ctgacgctgt cccagaagag gccgtacgtg gacgaggcgg agcggctgcg cctgcagcac      420
atgcaggact accccaacta caagtaccgg ccgcgcagga agaagcaggc caagcggctg      480
tgcaagcgcg tggacccggg cttccttctg agctccctct cccgggacca gaacgccctg      540
ccggagaaga gaagcggcag ccggggggcg ctgggggaga aggaggacag gggtgagtac      600 tccccccggca ctgccctgcc cagcctccgg ggctgctacc acgaggggcc ggctggtggt      660
ggcggcggcg gcaccccgag cagtgtggac acgtacccgt acgggctgcc cacacctcct      720
gaaatgtctc ccctggacgt gctggagccg gagcagacct tcttctcctc ccctgccag       780 gaggagcatg gccatcccg ccgcatccc cacctgccag ggcacccgta ctcaccggag        840
tacgccccaa gccctctcca ctgtagccac cccctgggct ccctggccct tggccagtcc      900
cccggcgtct ccatgatgtc ccctgtaccc ggctgtcccc catctcctgc ctattactcc      960
ccggccacct accacccact ccactccaac ctccaagccc acctgggcca gctttccccg      1020
cctcctgagc accctggctt cgacgccctg gatcaactga gccaggtgga actcctgggg      1080
gacatggatc gcaatgaatt cgaccagtat ttgaacactc ctggccaccc agactccgcc      1140
```

-continued

```
acagggggcca tggccctcag tgggcatgtt ccggtctccc aggtgacacc aacgggtccc      1200
acagagacca gcctcatctc cgtcctggct gatgccacgg ccacgtacta caacagctac      1260
agtgtgtcag gatcccccaa gaagaagagg aaagtctcga gcgactagaa agaccatgac      1320
ggtgattata aagatcatga catcgattac aaggatgacg atgacaaggc aagcttgcag      1380
gatgaccggt catcatcacc atcaccattg agt                                    1413

<210> SEQ ID NO 11
<211> LENGTH: 2106
<212> TYPE: DNA
<213> ORGANISM: Artificial Sequence
<220> FEATURE:
<223> OTHER INFORMATION: Tpase RNA coding sequence

<400> SEQUENCE: 11
gggagagccg ccaccatgga ggaagtatgt gattcatcag cagctgcgag cagcacagtc        60
caaaatcagc cacaggatca agagcacccg tggccgtatc ttcgcgaatt cttttctttta      120 agtggtgtaa ataaagattc attcaagatg aaatgtgtcc tctgtctccc gcttaataaa      180
gaaatatcgg ccttcaaaag ttcgccatca aacctaagga agcatattga gagaatgcac      240
ccaaattacc tcaaaaacta ctctaaattg acagcacaga agagaaagat cgggacctcc      300
acccatgctt ccagcagtaa gcaactgaaa gttgactcag ttttcccagt caaacatgtg      360
tctccagtca ctgtgaacaa agctatatta aggtacatca ttcaaggact tcatcctttc      420
agcactgttg atctgccatc atttaaagag ctgattagta cactgcagcc tggcatttct      480
gtcattacaa ggcctacttt acgctccaag atagctgaag ctgctctgat catgaaacag      540
aaagtgactg ctgccatgag tgaagttgaa tggattgcaa ccacaacgga ttgttggact      600
gcacgtagaa agtcattcat tggtgtaact gctcactgga tcaaccctgg aagtcttgaa      660
agacattccg ctgcacttgc ctgcaaaaga ttaatgggct ctcatacttt tgaggtactg      720
gccagtgcca tgaatgatat ccactcagag tatgaaatac gtgacaaggt tgtttgcaca      780
accacagaca gtggttccaa ctttatgaag gctttcagag ttttttggtgt ggaaaacaat      840 gatatcgaga ctgaggcaag aaggtgtgaa agtgatgaca ctgattctga aggctgtggt      900
gagggaagtg atggtgtgga attccaagat gcctcacgag tcctggacca agacgatggc      960
ttcgaattcc agctaccaaa acatcaaaag tgtgcctgtc acttacttaa cctagtctca     1020
agcgttgatg cccaaaaagc tctctcaaat gaacactaca agaaactcta cagatctgtc     1080
tttggcaaat gccaagcttt atggaataaa agcagccgat cggctctagc agctgaagct     1140
gttgaatcag aaagccggct tcagctttta aggccaaacc aaacgcggtg gaattcaact     1200
tttatggctg ttgacagaat tcttcaaatt tgcaaagaag caggagaagg cgcacttcgg     1260
aatatatgca cctctcttga ggttccaatg tttaatccag cagaaatgct gttcttgaca     1320
gagtgggcca acacaatgcg tccagttgca aaagtactcg acatcttgca agcggaaacg     1380
aatacacagc tggggtggct gctgcctagt gtccatcagt taagcttgaa acttcagcga     1440
ctccaccatt ctctcaggta ctgtgaccca cttgtggatg ccctacaaca aggaatccaa     1500
acacgattca agcatatgtt tgaagatcct gagatcatag cagctgccat ccttctccct     1560
aaatttcgga cctcttggac aaatgatgaa accatcataa aacgaggcat ggactacatc     1620
agagtgcatc tggagccttt ggaccacaag aaggaattgg ccaacagttc atctgatgat     1680
gaagattttt tcgcttcttt gaaaccgaca acacatgaag ccagcaaaga gttggatgga     1740
tatctggcct gtgtttcaga caccagggag tctctgctca cgtttcctgc tatttgcagc     1800
```

```
ctctctatca agactaatac acctcttccc gcatcggctg cctgtgagag gcttttcagc      1860
actgcaggat tgcttttcag ccccaaaaga gctaggcttg acactaacaa ttttgagaat      1920
cagcttctac tgaagttaaa tctgaggttt tacaactttg agggatcccc caagaagaag      1980
aggaaagtct cgagcgacta gaaagaccat gacggtgatt ataaagatca tgacatcgat      2040
tacaaggatg acgatgacaa ggcaagcttg caggatgacc ggtcatcatc accatcacca      2100
ttgagt                                                                 2106
```

```
<210> SEQ ID NO 12
<211> LENGTH: 915
<212> TYPE: DNA
<213> ORGANISM: Artificial Sequence
<220> FEATURE:
<223> OTHER INFORMATION: copGFP RNA coding sequence

<400> SEQUENCE: 12
gggagagccg ccaccatgga gagcgacgag agcggcctgc ccgccatgga gatcgagtgc        60
cgcatcaccg cacccctgaa cggcgtggag ttcgagctgg tgggcggcgg agagggcacc       120
cccaagcagg gccgcatgac caacaagatg aagagcacca aaggcgccct gaccttcagc       180
ccctacctgc tgagccacgt gatgggctac ggcttctacc acttcggcac ctaccccagc       240
ggctacgaga accccttcct gcacgccatc aacaacggcg ctacaccaa cacccgcatc        300 gagaagtacg aggacggcgg cgtgctgcac gtgagcttca gctaccgcta cgaggccggc       360
cgcgtgatcg gcgacttcaa ggtggtgggc accggcttcc ccgaggacag cgtgatcttc       420
accgacaaga tcatccgcag caacgccacc gtggagcacc tgcaccccat gggcgataac       480
gtgctggtgg gcagcttcgc ccgcaccttc agcctgcgcg acggcggcta ctacagcttc       540
gtggtggaca gccacatgca cttcaagagc gccatccacc ccagcatcct gcagaacggg       600
ggccccatgt tcgccttccg ccgcgtggag gagctgcaca gcaacaccga gctgggcatc       660
gtggagtacc agcacgcctt caagacccc atcgccttcg ccagatcccg cgctcagtcg        720
tccaattctg ccgtggacgg caccgccgga cccggctcca ccggatctcg cggatccccc       780
aagaagaaga ggaaagtctc gagcgactag aaagaccatg acggtgatta taaagatcat       840
gacatcgatt acaaggatga cgatgacaag gcaagcttgc aggatgaccg gtcatcatca       900
ccatcaccat tgagt                                                       915
```

```
<210> SEQ ID NO 13
<211> LENGTH: 6
<212> TYPE: PRT
<213> ORGANISM: Artificial Sequence
<220> FEATURE:
<223> OTHER INFORMATION: His tag

<400> SEQUENCE: 13

His His His His His His
1               5
```

```
<210> SEQ ID NO 14
<211> LENGTH: 26
<212> TYPE: PRT
<213> ORGANISM: Artificial Sequence
<220> FEATURE:
<223> OTHER INFORMATION: Calmodulin tag

<400> SEQUENCE: 14

Lys Arg Arg Trp Lys Lys Asn Phe Ile Ala Val Ser Ala Ala Asn Arg
```

```
1               5                10               15

Phe Lys Lys Ile Ser Ser Ser Gly Ala Leu
           20               25

<210> SEQ ID NO 15
<211> LENGTH: 8
<212> TYPE: PRT
<213> ORGANISM: Artificial Sequence
<220> FEATURE:
<223> OTHER INFORMATION: FLAG tag

<400> SEQUENCE: 15

Asp Tyr Lys Asp Asp Asp Asp Lys
1               5

<210> SEQ ID NO 16
<211> LENGTH: 9
<212> TYPE: PRT
<213> ORGANISM: Artificial Sequence
<220> FEATURE:
<223> OTHER INFORMATION: HA tag

<400> SEQUENCE: 16

Tyr Pro Tyr Asp Val Pro Asp Tyr Ala
1               5

<210> SEQ ID NO 17
<211> LENGTH: 15
<212> TYPE: PRT
<213> ORGANISM: Artificial Sequence
<220> FEATURE:
<223> OTHER INFORMATION: Avi tag

<400> SEQUENCE: 17

Gly Leu Asn Asp Ile Phe Glu Ala Gln Lys Ile Glu Trp His Glu
1               5                10               15

<210> SEQ ID NO 18
<211> LENGTH: 10
<212> TYPE: PRT
<213> ORGANISM: Artificial Sequence
<220> FEATURE:
<223> OTHER INFORMATION: Myc tag

<400> SEQUENCE: 18

Glu Gln Lys Leu Ile Ser Glu Glu Asp Leu
1               5                10

<210> SEQ ID NO 19
<211> LENGTH: 15
<212> TYPE: PRT
<213> ORGANISM: Artificial Sequence
<220> FEATURE:
<223> OTHER INFORMATION: S tag

<400> SEQUENCE: 19

Lys Glu Thr Ala Ala Ala Lys Phe Glu Arg Gln His Met Asp Ser
1               5                10               15

<210> SEQ ID NO 20
<211> LENGTH: 38
<212> TYPE: PRT
<213> ORGANISM: Artificial Sequence
<220> FEATURE:
<223> OTHER INFORMATION: SBP tag

<400> SEQUENCE: 20
```

-continued

```
Met Asp Glu Lys Thr Thr Gly Trp Arg Gly Gly His Val Val Glu Gly
1               5                   10                  15

Leu Ala Gly Glu Leu Glu Gln Leu Arg Ala Arg Leu Glu His His Pro
            20                  25                  30

Gln Gly Gln Arg Glu Pro
        35

<210> SEQ ID NO 21
<211> LENGTH: 13
<212> TYPE: PRT
<213> ORGANISM: Artificial Sequence
<220> FEATURE:
<223> OTHER INFORMATION: Softag 1

<400> SEQUENCE: 21

Ser Leu Ala Glu Leu Leu Asn Ala Gly Leu Gly Gly Ser
1               5                   10

<210> SEQ ID NO 22
<211> LENGTH: 8
<212> TYPE: PRT
<213> ORGANISM: Artificial Sequence
<220> FEATURE:
<223> OTHER INFORMATION: Softag 3

<400> SEQUENCE: 22

Thr Gln Asp Pro Ser Arg Val Gly
1               5

<210> SEQ ID NO 23
<211> LENGTH: 14
<212> TYPE: PRT
<213> ORGANISM: Artificial Sequence
<220> FEATURE:
<223> OTHER INFORMATION: V5 tag

<400> SEQUENCE: 23

Gly Lys Pro Ile Pro Asn Pro Leu Leu Gly Leu Asp Ser Thr
1               5                   10

<210> SEQ ID NO 24
<211> LENGTH: 8
<212> TYPE: PRT
<213> ORGANISM: Artificial Sequence
<220> FEATURE:
<223> OTHER INFORMATION: Xpress tag

<400> SEQUENCE: 24

Asp Leu Tyr Asp Asp Asp Asp Lys
1               5

<210> SEQ ID NO 25
<211> LENGTH: 16
<212> TYPE: PRT
<213> ORGANISM: Artificial Sequence
<220> FEATURE:
<223> OTHER INFORMATION: Isopeptag

<400> SEQUENCE: 25

Thr Asp Lys Asp Met Thr Ile Thr Phe Thr Asn Lys Lys Asp Ala Glu
1               5                   10                  15

<210> SEQ ID NO 26
<211> LENGTH: 13
<212> TYPE: PRT
```

-continued

```
<213> ORGANISM: Artificial Sequence
<220> FEATURE:
<223> OTHER INFORMATION: SpyTag

<400> SEQUENCE: 26

Ala His Ile Val Met Val Asp Ala Tyr Lys Pro Thr Lys
1               5                   10

<210> SEQ ID NO 27
<211> LENGTH: 8
<212> TYPE: PRT
<213> ORGANISM: Artificial Sequence
<220> FEATURE:
<223> OTHER INFORMATION: Streptactin tag (Strep-tag II)

<400> SEQUENCE: 27

Trp Ser His Pro Gln Phe Glu Lys
1               5

<210> SEQ ID NO 28
<211> LENGTH: 58
<212> TYPE: DNA
<213> ORGANISM: Artificial Sequence
<220> FEATURE:
<223> OTHER INFORMATION: VSW3-promoter Test (18)-F

<400> SEQUENCE: 28
ttaattgggc cacctatagt acacgggcag cttgccgggt tttagagcta gaaatagc        58

<210> SEQ ID NO 29
<211> LENGTH: 58
<212> TYPE: DNA
<213> ORGANISM: Artificial Sequence
<220> FEATURE:
<223> OTHER INFORMATION: VSW3-promoter Test (18)-R

<400> SEQUENCE: 29
gctatttcta gctctaaaac ccggcaagct gcccgtgtac tataggtggc ccaattaa        58

<210> SEQ ID NO 30
<211> LENGTH: 57
<212> TYPE: DNA
<213> ORGANISM: Artificial Sequence
<220> FEATURE:
<223> OTHER INFORMATION: VSW3-promoter Test (17)-F

<400> SEQUENCE: 30
taattgggcc acctatagta cacgggcagc ttgccgggtt ttagagctag aaatagc         57

<210> SEQ ID NO 31
<211> LENGTH: 57
<212> TYPE: DNA
<213> ORGANISM: Artificial Sequence
<220> FEATURE:
<223> OTHER INFORMATION: VSW3-promoter Test (17)-R

<400> SEQUENCE: 31
gctatttcta gctctaaaac ccggcaagct gcccgtgtac tataggtggc ccaatta         57

<210> SEQ ID NO 32
<211> LENGTH: 56
<212> TYPE: DNA
<213> ORGANISM: Artificial Sequence
<220> FEATURE:
<223> OTHER INFORMATION: VSW3-promoter Test (16)-F

<400> SEQUENCE: 32
```

-continued

```
aattgggcca cctatagtac acgggcagct tgccgggttt tagagctaga aatagc            56

<210> SEQ ID NO 33
<211> LENGTH: 56
<212> TYPE: DNA
<213> ORGANISM: Artificial Sequence
<220> FEATURE:
<223> OTHER INFORMATION: VSW3-promoter Test (16)-R

<400> SEQUENCE: 33
gctatttcta gctctaaaac ccggcaagct gcccgtgtac tataggtggc ccaatt          56

<210> SEQ ID NO 34
<211> LENGTH: 55
<212> TYPE: DNA
<213> ORGANISM: Artificial Sequence
<220> FEATURE:
<223> OTHER INFORMATION: VSW3-promoter Test (15)-F

<400> SEQUENCE: 34
attgggccac ctatagtaca cgggcagctt gccgggtttt agagctagaa atagc           55

<210> SEQ ID NO 35
<211> LENGTH: 55
<212> TYPE: DNA
<213> ORGANISM: Artificial Sequence
<220> FEATURE:
<223> OTHER INFORMATION: VSW3-promoter Test (15)-R

<400> SEQUENCE: 35
gctatttcta gctctaaaac ccggcaagct gcccgtgtac tataggtggc ccaat           55

<210> SEQ ID NO 36
<211> LENGTH: 54
<212> TYPE: DNA
<213> ORGANISM: Artificial Sequence
<220> FEATURE:
<223> OTHER INFORMATION: VSW3-promoter Test (14)-F

<400> SEQUENCE: 36
ttgggccacc tatagtacac gggcagcttg ccgggtttta gagctagaaa tagc            54

<210> SEQ ID NO 37
<211> LENGTH: 54
<212> TYPE: DNA
<213> ORGANISM: Artificial Sequence
<220> FEATURE:
<223> OTHER INFORMATION: VSW3-promoter Test (14)-R

<400> SEQUENCE: 37
gctatttcta gctctaaaac ccggcaagct gcccgtgtac tataggtggc ccaa            54

<210> SEQ ID NO 38
<211> LENGTH: 21
<212> TYPE: DNA
<213> ORGANISM: Artificial Sequence
<220> FEATURE:
<223> OTHER INFORMATION: Promoter

<400> SEQUENCE: 38
ttaattgggc cacctatagt a                                                21

<210> SEQ ID NO 39
<211> LENGTH: 25
<212> TYPE: DNA
```

<213> ORGANISM: Artificial Sequence
<220> FEATURE:
<223> OTHER INFORMATION: Trans_Template-cas9-F primer

<400> SEQUENCE: 39
agctggttta gtgaaccgtc agatc                                    25

<210> SEQ ID NO 40
<211> LENGTH: 26
<212> TYPE: DNA
<213> ORGANISM: Artificial Sequence
<220> FEATURE:
<223> OTHER INFORMATION: Trans_Template-cas9-R primer

<400> SEQUENCE: 40
actcaatggt gatggtgatg atgacc                                   26

<210> SEQ ID NO 41
<211> LENGTH: 23
<212> TYPE: DNA
<213> ORGANISM: Artificial Sequence
<220> FEATURE:
<223> OTHER INFORMATION: Primer

<400> SEQUENCE: 41
gtattgccta agcacagttt act                                      23

<210> SEQ ID NO 42
<211> LENGTH: 24
<212> TYPE: DNA
<213> ORGANISM: Artificial Sequence
<220> FEATURE:
<223> OTHER INFORMATION: sgRNA template-F

<400> SEQUENCE: 42
atcaggcgcc attcgccatt cagg                                     24

<210> SEQ ID NO 43
<211> LENGTH: 26
<212> TYPE: DNA
<213> ORGANISM: Artificial Sequence
<220> FEATURE:
<223> OTHER INFORMATION: sgRNA template-R

<400> SEQUENCE: 43
aaaaaaagca ccgactcggt gccact                                   26

<210> SEQ ID NO 44
<211> LENGTH: 25
<212> TYPE: DNA
<213> ORGANISM: Artificial Sequence
<220> FEATURE:
<223> OTHER INFORMATION: 3RACE-sgRNA-F-sgRNA primer

<400> SEQUENCE: 44
gcagcttgcc gggtttttaga gctag                                   25

<210> SEQ ID NO 45
<211> LENGTH: 22
<212> TYPE: DNA
<213> ORGANISM: Artificial Sequence
<220> FEATURE:
<223> OTHER INFORMATION: 3RACE-sgRNA R-sgRNA primer -continued

```
<400> SEQUENCE: 45
tagcccatca cgtggctcag ca                                                22
```